(12) United States Patent
Butler et al.

(10) Patent No.: US 7,745,221 B2
(45) Date of Patent: Jun. 29, 2010

(54) METHODS AND APPARATUS FOR SORTING CELLS USING AN OPTICAL SWITCH IN A MICROFLUIDIC CHANNEL NETWORK

(75) Inventors: William Frank Butler, La Jolla, CA (US); Mirianas Chachisvilis, San Diego, CA (US); Robert Dees, San Diego, CA (US); Norbert Hagen, Carlsbad, CA (US); Philippe Marchand, Poway, CA (US); Daniel E. Raymond, San Diego, CA (US); Eugene Tu, San Diego, CA (US); Mark M. Wang, San Diego, CA (US); Joon Mo Yang, San Diego, CA (US); Rong Yang, La Jolla, CA (US); Haichuan Zhang, San Diego, CA (US)

(73) Assignee: Celula, Inc., San Diego, CA (US)

( * ) Notice: Subject to any disclaimer, the term of this patent is extended or adjusted under 35 U.S.C. 154(b) by 1399 days.

(21) Appl. No.: 10/928,650

(22) Filed: Aug. 27, 2004

(65) Prior Publication Data
US 2005/0207940 A1    Sep. 22, 2005

Related U.S. Application Data

(60) Provisional application No. 60/499,294, filed on Aug. 28, 2003, provisional application No. 60/574,897, filed on May 26, 2004.

(51) Int. Cl.
*G01N 33/48* (2006.01)

(52) U.S. Cl. .................. 436/63; 422/68.1; 422/82.05; 422/100; 422/101; 422/102; 436/164; 436/165; 436/172; 436/180

(58) Field of Classification Search ............... 422/68.1, 422/82.05, 82.06, 82.07, 100, 101, 102; 436/63, 436/164, 165, 172, 177, 180; 385/12, 16
See application file for complete search history.

(56) References Cited

U.S. PATENT DOCUMENTS 3,558,877 A    1/1971    Pressman (Continued)

FOREIGN PATENT DOCUMENTS

DE    4326181 A1    2/1995

(Continued)

OTHER PUBLICATIONS

Ackerson et al, "Radiation Pressure As A Technique For Manipulating The Particle Order In Colloidal Suspensions", Faraday Discuss. Chem. Soc., 83, 1987, 309-316.

(Continued)

*Primary Examiner*—Jill Warden
*Assistant Examiner*—Dwayne K Handy
(74) *Attorney, Agent, or Firm*—David B. Murphy; O'Melveny & Myers LLP

(57) ABSTRACT

Apparatus and Methods are provided for a microfabricated fluorescence activated cell sorter based on an optical switch for rapid, active control of cell routing through a microfluidic channel network. This sorter enables low-stress, highly efficient sorting of populations of small numbers of cells (i.e., 1000-100,000 cells). The invention includes packaging of the microfluidic channel network in a self-contained plastic cartridge that enables microfluidic channel network to macro-scale instrument interconnect, in a sterile, disposable format.

32 Claims, 33 Drawing Sheets

U.S. PATENT DOCUMENTS

| | | |
|---|---|---|
| 3,628,182 A | 12/1971 | Ashkin et al. |
| 3,638,139 A | 1/1972 | Ashkin et al. |
| 3,662,183 A | 5/1972 | Ashkin et al. |
| 3,710,279 A | 1/1973 | Ashkin |
| 3,725,810 A | 4/1973 | Ashkin et al. |
| 3,761,721 A | 9/1973 | Altshuler et al. |
| 3,778,612 A | 12/1973 | Ashkin |
| 3,793,541 A | 2/1974 | Ashkin et al. |
| 3,808,432 A | 4/1974 | Ashkin |
| 3,808,550 A | 4/1974 | Ashkin |
| 3,826,899 A | 7/1974 | Ehrlich et al. |
| 4,063,106 A | 12/1977 | Ashkin et al. |
| 4,092,535 A | 5/1978 | Ashkin et al. |
| 4,127,329 A | 11/1978 | Chang et al. |
| 4,247,815 A | 1/1981 | Larson et al. |
| 4,253,846 A | 3/1981 | Smythe et al. |
| 4,327,288 A | 4/1982 | Ashkin et al. |
| 4,386,274 A | 5/1983 | Altshuler |
| 4,390,403 A | 6/1983 | Batchelder |
| 4,440,638 A | 4/1984 | Judy et al. |
| 4,451,412 A | 5/1984 | Loiseaux et al. |
| 4,453,805 A | 6/1984 | Ashkin et al. |
| 4,520,484 A | 5/1985 | Huignard et al. |
| 4,536,657 A | 8/1985 | Bruel |
| 4,627,689 A | 12/1986 | Asher |
| 4,632,517 A | 12/1986 | Asher |
| 4,756,427 A | 7/1988 | Göhde et al. |
| 4,827,125 A | 5/1989 | Goldstein |
| 4,886,360 A | 12/1989 | Finlan |
| 4,887,721 A | 12/1989 | Martin et al. |
| 4,893,886 A | 1/1990 | Ashkin |
| 4,908,112 A | 3/1990 | Pace |
| 4,939,081 A | 7/1990 | Figdor et al. |
| 5,029,791 A | 7/1991 | Ceccon et al. |
| 5,079,169 A | 1/1992 | Chu et al. |
| 5,100,627 A | 3/1992 | Buican et al. |
| 5,113,286 A | 5/1992 | Morrison |
| 5,121,400 A | 6/1992 | Verdiell et al. |
| 5,170,890 A | 12/1992 | Wilson et al. |
| 5,189,294 A | 2/1993 | Jackson et al. |
| 5,198,369 A | 3/1993 | Itoh et al. |
| 5,206,504 A | 4/1993 | Sridharan |
| 5,212,382 A | 5/1993 | Sasaki et al. |
| 5,245,466 A | 9/1993 | Burns et al. |
| 5,274,231 A | 12/1993 | Chu et al. |
| 5,283,417 A | 2/1994 | Misawa et al. |
| 5,308,976 A | 5/1994 | Misawa et al. |
| 5,327,515 A | 7/1994 | Anderson et al. |
| 5,337,324 A | 8/1994 | Ohtsu et al. |
| 5,338,930 A | 8/1994 | Chu et al. |
| 5,343,038 A | 8/1994 | Nishiwaki et al. |
| 5,355,252 A | 10/1994 | Haraguchi |
| 5,360,764 A | 11/1994 | Celotta et al. |
| 5,363,190 A | 11/1994 | Inaba et al. |
| 5,364,744 A | 11/1994 | Buican et al. |
| 5,374,556 A | 12/1994 | Bennett et al. |
| 5,445,011 A | 8/1995 | Ghislain et al. |
| 5,452,123 A | 9/1995 | Asher et al. |
| 5,472,550 A | 12/1995 | Periasamy |
| 5,473,471 A | 12/1995 | Yamagata et al. |
| 5,486,335 A * | 1/1996 | Wilding et al. ................ 422/55 |
| 5,495,105 A | 2/1996 | Nishimura et al. |
| 5,512,745 A | 4/1996 | Finer et al. |
| 5,608,519 A | 3/1997 | Gourley et al. |
| 5,620,857 A | 4/1997 | Weetall et al. |
| 5,625,484 A | 4/1997 | Coutsomitros |
| 5,629,802 A | 5/1997 | Clark |
| 5,631,141 A | 5/1997 | Sonek et al. |
| 5,637,458 A | 6/1997 | Frankel et al. |
| 5,644,588 A | 7/1997 | Misawa |
| 5,653,859 A | 8/1997 | Parton et al. |
| 5,659,561 A | 8/1997 | Torruellas et al. |
| 5,677,286 A | 10/1997 | Shull et al. |
| 5,689,109 A | 11/1997 | Schutze |
| 5,694,216 A | 12/1997 | Riza |
| 5,752,606 A | 5/1998 | Wilson et al. |
| 5,760,395 A | 6/1998 | Johnstone |
| 5,770,856 A | 6/1998 | Fillard et al. |
| 5,773,298 A | 6/1998 | Lynggaard et al. |
| 5,776,674 A | 7/1998 | Ulmer |
| 5,793,485 A | 8/1998 | Gourley |
| 5,795,457 A | 8/1998 | Pethig et al. |
| 5,804,436 A | 9/1998 | Okun et al. |
| 5,814,200 A | 9/1998 | Pethig et al. |
| 5,834,208 A | 11/1998 | Sakano |
| 5,858,192 A | 1/1999 | Becker et al. |
| 5,888,370 A | 3/1999 | Becker et al. |
| 5,900,160 A | 5/1999 | Whitesides et al. |
| 5,919,646 A | 7/1999 | Okun et al. |
| 5,935,507 A | 8/1999 | Morito et al. |
| 5,939,716 A | 8/1999 | Neal |
| 5,942,443 A | 8/1999 | Parce et al. |
| 5,950,071 A | 9/1999 | Hammond et al. |
| 5,952,651 A | 9/1999 | Morito et al. |
| 5,953,166 A | 9/1999 | Shikano et al. |
| 5,956,106 A | 9/1999 | Petersen et al. |
| 5,993,630 A | 11/1999 | Becker et al. |
| 5,993,631 A | 11/1999 | Parton et al. |
| 5,993,632 A | 11/1999 | Becker et al. |
| 5,998,152 A | 12/1999 | Lynch et al. |
| 6,008,010 A | 12/1999 | Greenberger et al. |
| 6,015,714 A | 1/2000 | Baldarelli et al. |
| 6,033,546 A | 3/2000 | Ramsey |
| 6,055,106 A | 4/2000 | Grier et al. |
| 6,067,859 A | 5/2000 | Kas et al. |
| 6,071,394 A | 6/2000 | Cheng et al. |
| 6,078,681 A | 6/2000 | Silver |
| 6,082,205 A | 7/2000 | Zborowski et al. |
| 6,088,097 A | 7/2000 | Uhl |
| 6,088,376 A | 7/2000 | O'Brien et al. |
| 6,096,509 A | 8/2000 | Okun et al. |
| 6,111,398 A | 8/2000 | Graham |
| 6,121,603 A | 9/2000 | Hang et al. |
| 6,139,831 A | 10/2000 | Shivashankar et al. |
| 6,142,025 A | 11/2000 | Zborowski et al. |
| 6,143,535 A | 11/2000 | Palsson |
| 6,143,558 A | 11/2000 | Kopelman et al. |
| 6,149,789 A | 11/2000 | Benecke et al. |
| 6,156,576 A | 12/2000 | Allbritton et al. |
| 6,197,176 B1 | 3/2001 | Pethig et al. |
| 6,208,815 B1 | 3/2001 | Seidel et al. |
| 6,215,134 B1 | 4/2001 | O'Brien et al. |
| 6,221,654 B1 | 4/2001 | Quake et al. |
| 6,224,732 B1 | 5/2001 | Imasaka et al. |
| 6,242,209 B1 | 6/2001 | Ransom et al. |
| 6,280,960 B1 | 8/2001 | Carr |
| 6,280,967 B1 | 8/2001 | Ransom et al. |
| 6,287,758 B1 | 9/2001 | Okun et al. |
| 6,287,776 B1 | 9/2001 | Hefti et al. |
| 6,287,832 B1 | 9/2001 | Becker et al. |
| 6,287,874 B1 | 9/2001 | Hefti |
| 6,294,063 B1 | 9/2001 | Becker et al. |
| 6,338,968 B1 | 1/2002 | Hefti |
| 6,344,325 B1 | 2/2002 | Quake et al. |
| 6,355,491 B1 | 3/2002 | Zhou et al. |
| 6,387,331 B1 | 5/2002 | Hunter |
| 6,395,480 B1 | 5/2002 | Hefti |
| 6,399,397 B1 | 6/2002 | Zarling et al. |
| 6,408,878 B2 | 6/2002 | Unger et al. |
| 6,411,838 B1 | 6/2002 | Nordstrom et al. |
| 6,485,690 B1 * | 11/2002 | Pfost et al. .................. 422/102 |
| 6,485,905 B2 | 11/2002 | Hefti |
| 6,507,400 B1 | 1/2003 | Pina et al. |
| 6,514,722 B2 | 2/2003 | Palsson et al. |

| | | | |
|---|---|---|---|
| 6,518,056 B2 | 2/2003 | Schembri et al. |
| 6,534,308 B1 | 3/2003 | Palsson et al. |
| 6,540,895 B1 | 4/2003 | Spence et al. |
| 6,566,079 B2 | 5/2003 | Hefti |
| 6,624,940 B1 | 9/2003 | Grier et al. |
| 6,641,708 B1 | 11/2003 | Becker et al. |
| 6,642,018 B1 | 11/2003 | Koller et al. |
| 6,740,497 B2 | 5/2004 | Allbritton et al. |
| 6,744,038 B2 | 6/2004 | Wang et al. |
| 6,778,724 B2 | 8/2004 | Wang et al. |
| 6,784,420 B2 | 8/2004 | Wang et al. |
| 6,797,942 B2 | 9/2004 | Grier et al. |
| 6,815,664 B2 | 11/2004 | Wang et al. |
| 6,823,124 B1 | 11/2004 | Renn et al. |
| 6,833,542 B2 | 12/2004 | Wang et al. |
| 2002/0025529 A1 | 2/2002 | Quake et al. |
| 2002/0058332 A1 | 5/2002 | Quake et al. |
| 2003/0032204 A1 | 2/2003 | Walt et al. |

FOREIGN PATENT DOCUMENTS

| | | | |
|---|---|---|---|
| EP | 0635994 B1 | 9/1998 |
| EP | 0556748 B1 | 10/1998 |
| EP | 0898493 B1 | 1/2000 |
| JP | 03101419 A | 4/1991 |
| JP | 05088107 A | 4/1993 |
| JP | 05232398 A | 9/1993 |
| JP | 06123886 A | 5/1994 |
| JP | 06132000 A | 5/1994 |
| JP | 08234110 A | 9/1996 |
| JP | 09043434 A | 2/1997 |
| JP | 10048102 A | 2/1998 |
| JP | 10062332 A | 3/1998 |
| JP | 11218691 A | 8/1999 |
| WO | WO 94/08221 A1 | 4/1994 |
| WO | WO 97/21832 A1 | 6/1997 |
| WO | WO 99/39190 A1 | 8/1999 |
| WO | WO 99/61888 A2 | 12/1999 |
| WO | WO 00/23825 A2 | 4/2000 |
| WO | WO 00/45160 A1 | 8/2000 |
| WO | WO 00/45179 A2 | 8/2000 |
| WO | WO 01/05514 A1 | 1/2001 |
| WO | WO 01/09606 A1 | 2/2001 |
| WO | WO 01/11333 A2 | 2/2001 |
| WO | WO 01/14870 A1 | 3/2001 |
| WO | WO 01/20329 A2 | 3/2001 |
| WO | WO 01/32930 A1 | 5/2001 |
| WO | WO 01/40769 A2 | 6/2001 |
| WO | WO 01/44852 A2 | 6/2001 |
| WO | WO 01/68110 A1 | 9/2001 |
| WO | WO 02/22774 A1 | 3/2002 |
| WO | WO 02/39104 A1 | 5/2002 |
| WO | WO 02/44689 | * | 6/2002 |

OTHER PUBLICATIONS

Afzal, et al, "Optical Tweezers Using A Diode Laser", Rev. Sci. Instrum., 63, 4, Apr. 1992, 2157-2163.

Amato, "Optical Matter Emerges Under Laser", Science News, 136, 1989, 212.

Arlt, et al, "Moving Interference Patterns Created Using The Angular Doppler Effect", Optics Express, 10, 16, 202, 844-852.

Asher, et al, "Crystalline Colloidal Bragg Diffraction Devices: The Basis For A New Generation Of Raman Instrumentation", Spectroscopy, 1, 12, 1986, 26-31.

Ashkin, "Acceleration & Trapping Of Particles by Radiation Pressure", Physical Review Letters, 24, 4, Jan. 26, 1970, 156-159.

Ashkin, "Trapping Of Atoms By Resonance Radiation Pressure", Physical Review Letters, 40, 12, Mar. 20, 1978, 729-732.

Ashkin, "Applications Of Laser Radiation Pressure", Science, 210, 4474, Dec. 5, 1980, 1081-1088.

Ashkin, "Forces Of A Single Beam Gradient Laser Trap On A Dielectric Sphere In The Ray Optics Regime", Biophys.J., 61, Feb. 1992, 569-582.

Ashkin, et al., "Optical Levitation Of Liquid Drops By Radiation Pressure", Science, 187, 4181, Mar. 21, 1975, 1073-1075.

Ashkin, et al, "Observation Of A Single Beam Gradient Force Optical Trap For Dielectric Particles", Optics Letters, 11, 5, May 1986, 288-290.

Ashkin, et al, "Optical Trapping & Manipulation Of Viruses & Bacteria", Science, 235, 4795, Mar. 20, 1987, 1517-1520.

Ashkin, et al, "Optical Trapping & Manipulation Of Single Cells Using Infrared Laser Beams", Nature, 330, 6150, Dec. 24-31, 1987, 769-771.

Ashkin, et al, "Force Generation Of Organelle Transport Measured In Vivo By An Infrared Laser Trap", Nature, 348, Nov. 22, 1990, 346-348.

Ashkin, et al, "Internal Cell Manipulation Using Infrared Laser Traps", Proc. Natl. Acad. Sci. USA, 86, 20, Oct. 1989, 7914-7918.

Ashkin, et al., "Optical Levitation By Radiation Pressure", Appl. Phys.Lett., 19, 8, Oct. 15, 1971, 283-285.

Ashkin, "Optical Trapping & Manipulation Of Neutral Particles Using Lasers", Proc.Natl.Acad.Sci.USA, 94, 10, May 13, 1997, 4853-4860.

Ashkin, "The Pressure Of Laser Light", Scientific Amerian, 226, 2, 1972, 63-71.

Aviva website printout, www.avivabio.com.

Bagnato, et al, "Continuous Stopping & Trapping Of Neutral Atoms", Physical Review Letters, 58, 21, May 25, 1987, 2194-2197.

Becker, et al, "Separation Of Human Breast Cancer Cells From Blood By Differential Dielectric Affinity", Proc. Natl. Acad. Sci. USA, 92, Jan. 1995, 860-864.

Berns, et al, "Use Of A Laser Induced Optical Force Trap To Study Chromosome Movement On the Mitotic Spindle", Proc. Natl. Acad. Sci. USA, 86, 12, Jun. 1989, 4539-4543.

Berns, et al, "Laser Microbeam As A Tool In Cell Biology: A Survey Of Cell Biology", *International Review of Cytology*, 129, 1991, 1-44 (Academic Press: San Diego).

Biegelow, et al, "Observation Of Channeling Of Atoms In The Three Dimensional Interference Pattern Of Optical Standing Waves", Physical Review Letters, 65, 1, Jul. 2, 1990, 29-32.

Block, et al., "Compliance Of Bacterial Flagella Measurement Without Optical Tweezers", Nature, 338, 6215, Apr. 6, 1989, 514-518.

Block, "Optical Tweezers: A New Tool For Biophysics", *Noninvasive Techniques In Cell Biology*, chap 15, 1990, 375-402. (Wiley-Liss Inc.: New York).

Bronkhorst, et al, "A New Method To Study Shape Recovery Of Red Blood Cells Using Multiple Optical Trapping", Biophys. J., 69, 5, Nov. 1995, 1666-1673.

Buican et al., "Automated Single Cell Manipulation & Sorting By Light Trapping", Applied Optics, 26, 24, Dec. 15, 1987, 5311-5316.

Buican, "Automated Cell-Separation Techniques Based On Optical Trapping", ACS Symposium Series, 464, 1991, 59-72.

Burns, et al, "Optical Binding", Physical Review Letters, 63, 12, Sep. 18, 1989, 1233-1236.

Burns, et al., "Optical Matter. Crystallization & Binding In Intense Optical Fields", Science, 249, 4970, Aug. 17, 1990, 749-754.

Business Week, "Is There Anything A Laser Can't Do?", Business Week, Oct. 30, 1989, 157.

Bustamante, "Direct Observation & Manipulation Of Single DNA Molecules Using Fluorescence Microscopy", Annu. Rev. Biophys. Biophys. Chem., 20, 1991, 415-446.

Bustamante, et al., "Towards A Molecular Description Of Pulsed Field Gel Electrophoresis", Trends In Biotechnology, 11, 1993, 23-30.

Bustamante, et al., "Manipulation Of Single DNA Molecules & Measurement Of Their Persistence, Length & Charge Density Under A Fluorescence Microscope", Abst. Of the 19th Mtg. Of Annual Mtg. Of Amer. Soc. For Photobiology, 53, Jun. 22, 1991, 46S (Pergamon Press: Oxford).

Caldwell, "Field-Flow Fractionation", Analytical Chemistry, 60, 17, Sep. 1, 1988, 959-971.

Chiou, et al., "Interferometric Optical Tweezers", Optics Communications, 133, Jan. 1, 1997, 7-10.

Chou, et al, "A Microfabricated Device for Sizing & Sorting DNA Molecules", Proc. Natl. Acad. Sci. USA, 96, Jan. 1999, 11-13.

Chowdhury, et al., "Laser Induced Freezing", Physical Review Letters, 55, 8, Aug. 19, 1985, 833-836.
Chowdhury, et al., "All Optical Logic Gates Using Colloids", Microwave & Optical Technology Letters, 1, 5, Jul. 1988, 175-178.
Chowdhury, et al., Exchange of Letters, Science, 252, May 24, 1991.
Chu, et al., "Experimental Observation of Optically Trapped Atoms", Physical Review Letters, 57, 3, Jul. 21, 1986, 314-317.
Clark, et al., "Single Colloidal Crystals", Nature, 281, 5726, Sep. 6, 1979, 57-60.
Clark, J.M. and Switzer, R.L., eds., *Experimental Biochemistry 2nd Edition*, Section II, W.H. Freeman and Co., New York 1997, 73-74.
Crocker, et al., Microscopic Measurement Of The Pair Interaction Potential Of Charge Stabilized Colloid, Physical Review Letters, 73, 2, Jul. 11, 1994, 352-355.
Cromie, "Scientists Bind Matter With Light", Harvard University Gazette, Oct. 13, 1989, 1, 4-5.
Davies, et al, "Optically Controlled Collisions Of Biological Objects", SPIE, 3260, Jan. 25-28, 1998, 15-22.
Dholakia, et al, "Optical Tweezers: The Next Generation", Physics World, Oct. 2002, 31-35.
Dufresne, et al, "Optical Tweezer Arrays & Optical Substrates Created With Diffractive Optics", Review Of Scientific Instruments, 69, 5, May 1998, 1974-1977.
Esener, Center For Chips With Heterogeneously Integrated Photonics (CHIPS), DARPA Opto Centers Kickoff, Nov. 8, 2000, Dana Point, CA.
Fallman, et al., "Design For Fully Steerable Dual Trap Optical Tweezers", Applied Optics, 36, 10, Apr. 1, 1997, 2107-2113.
Fisher, "The Light That Binds", Popular Science, Jan. 1990, 24-25.
Flynn, et al, "Parallel Transport Of Biological Cells Using Individually Addressable VCSEL Arrays As Optical Tweezers", Sensors & Actuators B, 87, 2002, 239-243.
Fournier, et al., "Writting Diffractive Structures By Optical Trapping", SPIE, 2406, Feb. 6-8, 1995, 101-112.
Fu, et al, "A Microfabricated Fluorescence Activated Cell Sorter", Nature Biotechnology, 17, Nov. 1999, 1109-1111.
Fuhr, et al., "Force Measurements Of Optical Tweezers In Electro-Optical Cages", Appl. Physics A, A67, (4), 1998, 385-390.
Gascoyne, website printout, Dec. 1, 2000.
Gorre-Talini, et al, "Sorting Of Brownian Particles By The Pulsed Application Of A Asymmetric Potential", Physical Review E, 56, 2, Aug. 1997, 2025-2034.
Grier, "New Age Crystals", Nature, 389, 6653, Oct. 23, 1997, 784-785.
Greulich, et al, "The Light Microscope On Its Way From An Analytical To A Preparative Tool", Journal Of Microscopy, 167, Pt. 2, Aug. 1, 1992, 127-151.
Grover, et al, "Automated Single-Cell Sorting System Based On Optical Trapping", Journal of Biomedical Optics, 6, 1, Jan. 2001, 14-22.
Gurrieri, et al, "Imaging Of Kinked Configurations Of DNA Molecules Undergoing Orthogonal Field Alternating Gel Electrophoresis By Fluorescence Microscope", Biochemistry, 29, 13, Apr. 3, 1990, 3396-3401.
Gurrieri, et al. Trapping Of Megabase Sized DNA Molecules During Agarose Gel Electrophoresis, Proc. Natl. Acad. Sci. USA, 96, Jan. 1999, 453-458.
Holtz, et al, "Polymerized Colloidal Crystal Hydrogel Films As Intelligent Chemical Sensing Materials", Nature, 389, Oct. 23, 1997, 829-832.
Houseal, et al, "Imaging Of The Motions & Conformational Transitions Of Single DNA Molecules Using Fluorescence Microscopy", Biophys.J., 55, 324, Feb. 12-16, 1989, 373a.
Houseal, et al., "Real Time Imaging Of Single DNA Molecules With Fluorescence Microscopy", Biophys.J., 56, Sep. 1989, 507-516.
Huber, et al., "Isolation Of A Hyperthermophilic Archaeum Predicted By in situ RNA Analysis", Nature, 376, 6535, Jul. 6, 1995, 57-58.
Imasaka, et al., "Optical Chromatography", Analytical Chemistry, 67, 11, Jun. 1, 1995, 1763-1765.
Imasaka, et al., "Optical Chromatography. A New Tool For Separation Of Particles", Analusis, 26, 5, 1998, M53-M55.

Inside R&D, "Matter Bound By Light", Inside R&D, 18, 43, Oct. 25, 1989, 2.
Kuo, et al., "Optical Tweezers In Cell Biology", Trends In Cell Biology, 2, Apr. 1992, 116-118.
Lai, Determination Of Spring Constant Of Laser Trapped Particle By Self-Mining Interferometry, Proc. Of SPIE, 3921, 2000, 197-204.
Law, "Matter Rides On Ripples Of Light", New Scientist, 1691, Nov. 18, 1989, 1691.
Leger, et al, "Coherent Laser Addition Using Binary Phase Gratings", Applied Optics, 26, 20, Oct. 15, 1987, 4391-4399.
Macdonald, et al., "Trapping & Manipulation Of Low Index Particles In A Two-Dimensional Interferometric Optical Trap", Optics Letters, 26, 12, 2001, 863-865.
Mammen, et al, "Optically Controlled Collisions Of Biological Objects To Evaluate Potent Polyvalent Inhibitors Of Virus-Cell Adhesion", Chemistry & Biology, 3, 9, Sep. 1996, 757-763.
Markx et al, "The Dielectrophoretic Levitation Of Latex Beads, with Reference To Field-Flow Fractionation", Journal of Physics D: Applied Physics, 30, 17, 2470-2477.
Markx, et al., "Dielectrophoretic Separation Of Bacterial Using A Conductivity Gradient", Journal Of Biotechnology, 51, 1996, 175-180.
Mason, et al, "Optical Measurements Of Frequency Dependent Linear Viscoelastic Moduli Of Complex Fluids", Physical Review Letters, 74, 7, Feb. 13, 1995, 1250-1253.
McClelland, et al, "Low Frequency Peculiarities Of The Photorefractive Response In Sillenites", Optics Communications, 113, Jan. 1, 1995, 371-377.
Misawa, et al, "Spatial Pattern Formation, Size Selection, & Directional Flow Of Polymer Latex Particles By Laser Trapping Technique", Chemistry Letters, 3, Mar. 1991, 469-472.
Misawa, et al, "Multibeam Laser Manipulation & Fixation Of Microparticles", Appl.Phys.Lett., 60, 3, Jan. 20, 1992, 310-312.
Mitchell, et al, "A Practical Optical Trap For Manipulating & Isolating Bacterial from Complex Microbial Communities", Microb.Ecol., 25, 2, 1993, 113-119.
Molloy, et al., "Lights, Action: Optical Tweezers", Contemp. Physics, 43, 4, 2001, 241-248.
Molloy, et al., "Optical Tweezers In A New Light", J. Modern Optics, 50, 10, 2003, 1501-1507.
Murray, et al, "Experimental Observation Of Two Stage Melting In A Classical Two Dimensional Screened Coulomb System", Physical Review Letters, 58, 12, Mar. 23, 1987, 1200-1203.
Murray, et al, "Colloidal Crystals", American Scientist, 83, 3, May-Jun. 1995, 238-245.
Mycometrix, website printout, www.mycometrix.com, Dec. 1, 2000.
New York Times, "Atoms Bound Together By Light", New York Times, Oct. 31, 1989, C17.
Paterson, et al, "Controlled Rotation Of Optically Trapped Microscopic Particles", Science, 292, May 4, 2001, 912-914.
Pethig, et al., "Applications Of Dielectrophoresis In Biotechnology", Trends Biotechnol., 15, 10, 1997, 426-432.
Prieve, et al., "Use of Optical Forces To Detach Single Microscopic Particles Adhering To Flat Surfaces In Aqueous Media", Proceedinsgs of the Annual Meeting of the Adhesion Society, 20th, 1997, 151-153.
Pritchard, et al., "Light Traps Using Spontaneous Forces", Physical Review Letters, 57, 3, Jul. 21, 1986, 310-313.
Quake, et al, "From Micro- to Nanofabrication With Soft Materials", Science, 290, Nov. 24, 2000, 1536-1540.
Raab, et al, "Trapping Of Neutral Sodium Atoms With Radiation Pressure", Physical Review Letters, 59, 23, Dec. 7, 1987, 2631-2634.
Rogovin, et al, "Bifurcation In Degenerate Four-Wave Mixing In Liquid Suspensions Of Microspheres", Physical Review Letters, 54, 20, May 20, 1985, 2222-2225.
Roosen, "A Theoretical & Experimental Study Of The Stable Equilibrium Positions Of Spheres Levitated By Two Horizontal Laser Beams", Optics Communications, 21, 1, Apr. 1977, 189-194.
Sasaki, et al, "Laser Scanning Micromanipulation & Spatial Patterning Of Fine Particles", Japanese Journal Of Applied Physics, 31, 5B, May 1991, L907-L909.

Sasaki, et al, "Pattern Formation & Flow Control Of Fine Particles By Laser Scanning Micromanipulation", Optics Letters, 16, 19, Oct. 1, 1991, 1463-1465.

Sasaki et al., "Optical Micromanipulation Of A Lasing Polymer Particle In Water", Japanese Journal Of Applied Physics, Pt. 2, 32, 8B, Aug. 15, 1993, L1144-L1147.

Sasaki, et al, "Optical Trapping Of A Metal Particle & A Water Droplet By A Scanning Laser Beam", Appl. Phys. Lett., 60, 7, Feb. 17, 1992, 807-809.

Shikano, et al, "Separation Of A Single Cell By Red-Laser Manipulation", Applied Physics Letters, 75, 17, Oct. 25, 1999, 2671-2673.

Smith, et al, "Four Wave Mixing In An Artificial Kerr Medium", Optics Letters, 6, 6, Jun. 1981, 284-286.

Smith, et al, "Direct Mechanical Measurements Of The Elasticity Of Single DNA Molecules By Using Magnetic Beads", Science, 258, 5085, Nov. 13, 1992, 1122-1126.

Smith, et al, "Model & Computer Simulations Of The Motion Of DNA Molecules During Pulsed Field Gel Electrophoresis", Biochemistry, 30, 21, May 28, 1991, 5264-5274.

Sonek, et al, "Micromanipulation & Physical Monitoring Of Cells Using Two-Photon Excited Fluorescence In CW Laser Tweezers", SPIE, 2678, Jan. 28-Feb. 1, 1996, 62-68.

Suzuki, et al, "Hysteric Behavior & Irreversibility Of Polymer Gels By pH Change", J. Chem. Phys., 103, 11, Sep. 15, 1995, 4706-4710.

Suzuki, et al., "Optical Switching In Polymer Gels", J. Appl. Phys., 80, 1, Jul. 1, 1996, 131-136.

Svoboda, et al, "Biological Applications In Optical Forces", Annu .Rev. Biophys. Biomol. Struct., 23, 1994, 247-285.

Svoboda, et al, Conformation & Elasticity Of The Isolated Red Blood Cell Membrane Skeleton, Biophys. J., 63, 3, Sep. 1, 1992, 784-793.

Swanson, et al, "Diffractive Optical Elements For Use In Infrared Systems", Optical Engineering, 28, 6, Jun. 1989, 605-608.

Takashima, et al., "Dielectric Dispersion Of DNA", J. Mol. Biol., 7, 5, Nov. 1963, 455-467.

Thirunamachandran, "Intramolecular Interactions In The Presence of An Intense Radiation Field", Molecular Physics, 40, 2, 1980, 393-399.

Tsai, et al., "Applications Of Optical Tweezers And An Integreted Force Measurement Module For Biomedical Research", Proceedings of the SPIE, 4082, Jul. 2000, 213-221.

Unger, et al, "Monolithic Microfabricated Valves & Pumps By Multilayer Soft Lithography", Science, 288, Apr. 7, 2000, 113-116.

vanBlaaderen, et al, "Template Directed Colloidal Crystallization", Nature, 385, 6614, Jan. 23, 1997, 321-324.

Visscher, et al, "Construction Of Multiple Beam Optical Traps With Nanometer Resolution Position Screening", IEEE Jnl Of Selected Topics In Quantum Electronics, 2, 4, Dec. 1996, 1066-1075.

Wang et al, "All Optical Switching Of Biological Samples In A Microfluidic Device", International Phonics Conference 2000, Dec. 12-15, 2000, Hsinchu, Taiwan.

Wang, et al, "Integration Of Optoelectronic Array Devices For Cell Transport & Sorting", Photonics West 2001, Jan. 20-26, 2001, San Jose, CA.

Weber, et al, "Manipulation Of Cells, Organelles & Genomes By Laser Microbeam & Optical Trap", Intl. Rev. Of Cytology, 133, 1992, 1-41, (Academic Press: San Diego).

Wei, et al, Laser Trapping Microscopy As A Diagnostic Technique For The Study Of Cellular Response & Laser-Cell Interactions, SPIE, 2983, Feb. 10-11, 1997, 22-28.

Westbrook, et al, "Localization Of Atoms In A Three Dimensional Standing Wave", Physical Review Letters, 65, 1, Jul. 2, 1990, 33-36.

Wheeler, "Force Fields Of Laser Light Bind Molecules In A Remarkable Discovery At Harvard", The Chronicle Of Higher Education, Oct. 25, 1989, A4.

Wright, et al, "Radiation Trapping Forces On Microspheres With Optical Tweezers", Appl. Phys. Lett., 63, 6, Aug. 9, 1993, 715-717.

Wuite, et al, "An Integrated Laser Trap/Flow Control Video Microscope For The Study Of Single Biomolecules", Biophys. Jnl., 79, 2, Aug. 2000, 1155-1167.

Xiang, et al, "A Combinatorial Approach To Materials Discovery", Science, 268, 5218, Jun. 23, 1995, 1738-1740.

Yablonovitch, "Inhibited Spontaneous Emission In Solid State Physics & Electronics", Physical Review Letters, 58, 20, May 18, 1987, 2059-2062.

Yablonovitch, et al, "Photonic Band Structure: The Face Centered Cubic Face", Physical Review Letters, 63, 18, Oct. 30, 1989, 1950-1953.

Yang, et al., "Dielectric Properties Of Human Leukocyte Subpopulations Determined By Electrorotation As A Cell Separation Criterion", Biophysical J., 76, 199, 3307-3314.

Yuqiu, "Mechanical, Electrical, & Chemical Manipulation Of Single DNA Molecules", Nanotechnology, 3, 1992, 16-20.

Zahn, et al, "Fluorimetric Multiparameter Cell Assay At The Single Cell Level Fabricated By Optical Tweezers", FEBS Letters, 443, 1999, 337-340.

Zemenek, et al., "Optical Trapping of Rayleight Particles Using A Gaussian Standing Wave", Optics Communication, 151, 4, 5, 6, 1998, 273-285.

* cited by examiner

Drawing is on a 0.5 mm grid.
All lines are 10 μm wide.

METHODS AND APPARATUS FOR SORTING CELLS USING AN OPTICAL SWITCH IN A MICROFLUIDIC CHANNEL NETWORK

RELATED APPLICATIONS

This application claims priority to U.S. Provisional Application Ser. No. 60/499,294, filed Aug. 28, 2003, entitled "Microsorter Cartridge" and U.S. Provisional application Ser. No. 60/574,897, filed May 26, 2004, entitled "Optical Switch to Enable Cell Sorting in a Microfluidic Channel Network", and are incorporated herein by reference as if fully set forth herein.

FIELD OF THE INVENTION

This invention relates to methods and apparatus for the use of optical forces in a microfluidic channel network to provide an optical switch that enables selective routing of target cells through the network to sort them from non-target cells and collect them.

BACKGROUND OF THE INVENTION

Conventional fluorescent activated cell sorters (FACS) are widely used in research and clinical applications[1]. These instruments are capable of very fast, multiparameter analysis and sorting but generally require large sample volumes, a trained operator for operation and maintenance, and are difficult to sterilize. FACS instruments are able to analyze as few as 10,000 and as many as tens of millions of cells. However, below 100,000 cells the ability to perform sorting diminishes[1]. Other separation methods such as magnetic beads don't require as many cells as FACS but they suffer from nonspecific binding, aggregation of cells and beads, and from the possibility that the beads themselves could interfere in subsequent processing steps. Thus, for sorting precious, small samples or cells from primary tissue, a cell sorter that is capable of handling small sample volumes with low cell numbers and that allows efficient recovery of the sorted populations addresses a unique scientific niche.

Microfabricated cytometers have the potential to sort with as few as 1,000 cells while concomitantly consuming less reagents in an easy to use, closed system. The latter is important because, unlike conventional FACS instruments, aerosols are not created, reducing the risks of contamination of the sorted cells and of working with biohazardous materials. Several microfabricated cell sorters have been described, but mostly as "proof of concept". Fu, et al.[2] reported 30-fold enrichment of *E. coli* at a throughput of 17 cells/s. Only 20% of the bacteria were viable after sorting and the sort purity in the target reservoir was 30%. In a subsequent study[3], the throughput increased to 44 cells/s but the target purity decreased to less than 10%, with recovery reported as 39%. Wolff, et al.[4] were able to sort beads from chicken red blood cells at a throughput of 12,000 events/s, with 100-fold enrichment. However, purity in the target well was about 1%. In these studies, enrichment was defined as the increase in the concentration of the target population in the collection well compared to the starting concentration. Purity referred to the accuracy of the sort and was the percentage of target cells sorted over all cells sorted into the collection well. Recovery was defined as the number of cells counted by the fluorescent detector vs. cells recovered from the collection well. The latter two studies used pressure switches in microfluidic devices that switched the entire fluid flow path and, consequently, any particles contained within the fluid plug. The mechanical compliance in these switches caused the fluid switch speed to be the rate limiting step for throughput[3]. Electrokinetic flow control has also been reported, e.g., electroosmosis[2,5,6] or dielectrophoresis[7,8,9], but the high electric field gradients and physicochemical restrictions on the ionic strength of the buffer are non-ideal conditions for cells.

Buican et al.[9] first proposed the use of optical forces for the deflection of particles through a fluidic channel. The force exerted on a particle by an optical beam is a function of the optical power and the relative optical properties of the particle and its surrounding fluid medium. Forces on the order of 1 pN/mW can be achieved for biological cells approximately 10 µm in diameter. While the optical force is small, the force necessary to deflect a cell into an adjacent flowstream is also small, e.g. 900 pN to move a 10 µm diameter cell, 20-40 µm laterally across the flow in a few milliseconds. This is the force necessary to overcome the viscous drag force on the cell at the velocity implied by this lateral motion.

The principles behind the optical forces and general background technology may be found in U.S. Pat. No. 6,744,038, which is incorporated herein by reference as if fully set forth herein.

SUMMARY OF THE INVENTION

As described below, these optical forces are used to realize an optical switch in a microfluidic channel network, operable as a cell sorting system. The optical switch is triggered by detection of a fluorescence signal from target cells flowing in the microfluidic channel network upstream of the optical switch position, although other detection modalities such as light scattering could equally be used for activation of the optical switch. The optical switch is used to direct cells or particles into one of a multiple number of output channel flow streams without modifying the underlying flow, whereby the desired cells are collected for further use. It is important that the flow in a microfluidic channel is typically laminar at a very low Reynolds number. Consequently, any cell flowing in a particular lamina, or flow stream, will stay in that flow stream in the absence of any forces transverse to the lamina. The optical switch utilizes optical forces on a cell to accomplish just this, the transport of cells transverse to the lamina to move the cells from a flow stream that exits a bifurcation junction through one output channel to a flow stream that exits the bifurcation junction through the second output channel.

The invention described in the following paragraphs details the methodology used to create an optical switch and the approaches used to optimize the optical switch, the design of the microfluidic channel network and the properties of the flow of cells or particles in the microfluidic network in order to achieve enhanced sorting performance. The optical switch generally works by projecting an optical illumination field into the microfluidic channel network in the vicinity of the cell's trajectory in an established flow in a microfluidic channel. The interaction of the cell with the optical field produce forces on the cell that transport it transverse to the established flow such that it moves from one flowstream to another flowstream in the established flow, without trapping the cell or significantly altering its motion in the primary flow.

In the following text the terms cells and particles both will be understood to mean any of biological cells, biological particles, natural organic or inorganic particles and man-made organic or inorganic particles. The size range of the cells sorted in the microfluidic channel network is typically that of biological cells, with diameters ranging from approximately 1 µm to approximately 50 µm. More generally, cells with diameters ranging from approximately 100 nm to approximately 100 µm are candidates for sorting by means of an optical switch in a microfluidic channel network.

Also, in general a laser has been used to produce the optical beam used in the optical switch. The laser currently used for the optical switch is a near-IR, continuous wave laser that is known not to harm the viability of biological cells at the power densities and exposure times used to demonstrate optical switching. Alternate laser sources may be considered for different applications, including visible or near-UV wavelength lasers if damage to the particles is not an issue, or pulsed lasers where a large flux of light can be used to move the particle very quickly. However, the source of the optical beam does not need to be limited to a laser, even though further discussion of the invention uses a laser to produce the optical switch.

[Note that in subsequent figures text based labeling has been used instead number based labeling; nevertheless, in similar figures the number based labeling of FIGS. 1-4 still applies.]

Figure 5:
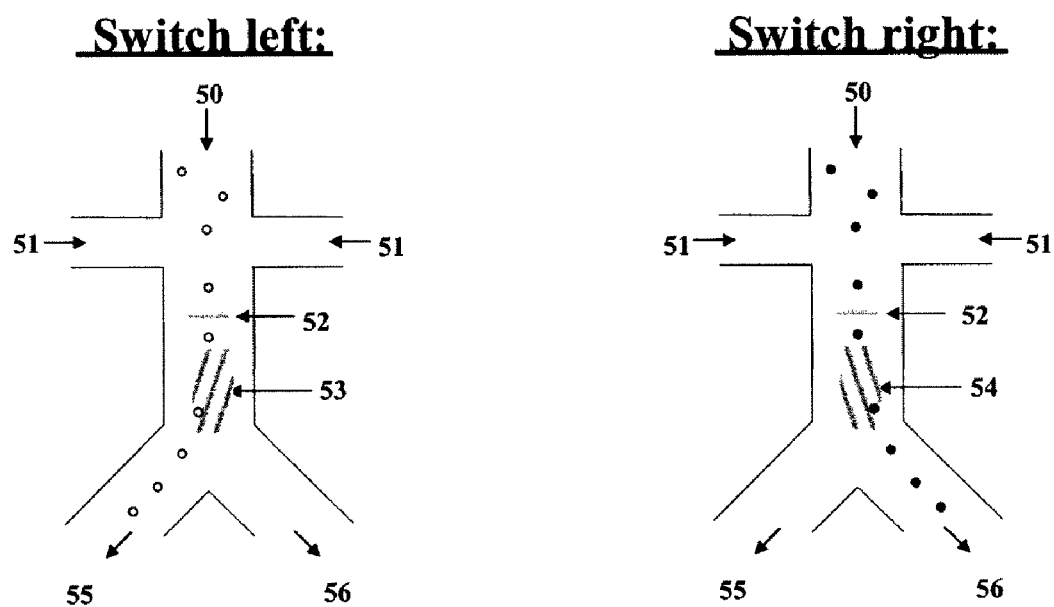

FIG. 5 is a 50/50 optical switch network with a bi-directional laser line optical switch.

Figure 6:
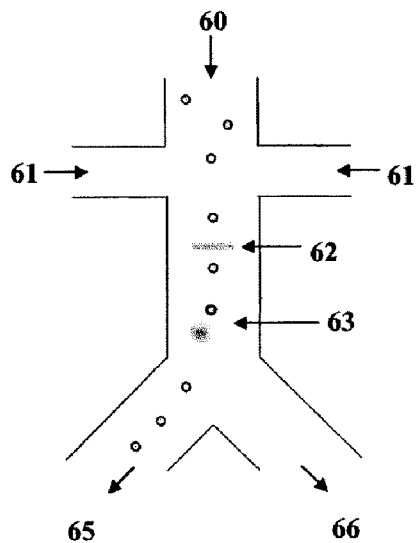
Figure 6:
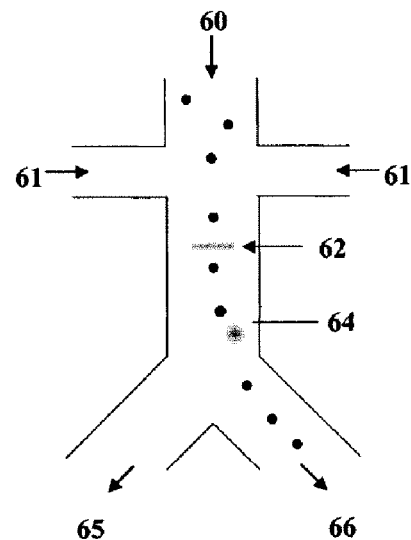

FIG. 6 is a 50/50 optical switch network with a bi-directional laser spot optical switch.

FIG. 7 is a plan view of laser line optical switches in larger microfluidic channel networks with more than two outlet channels.

Figure 8:
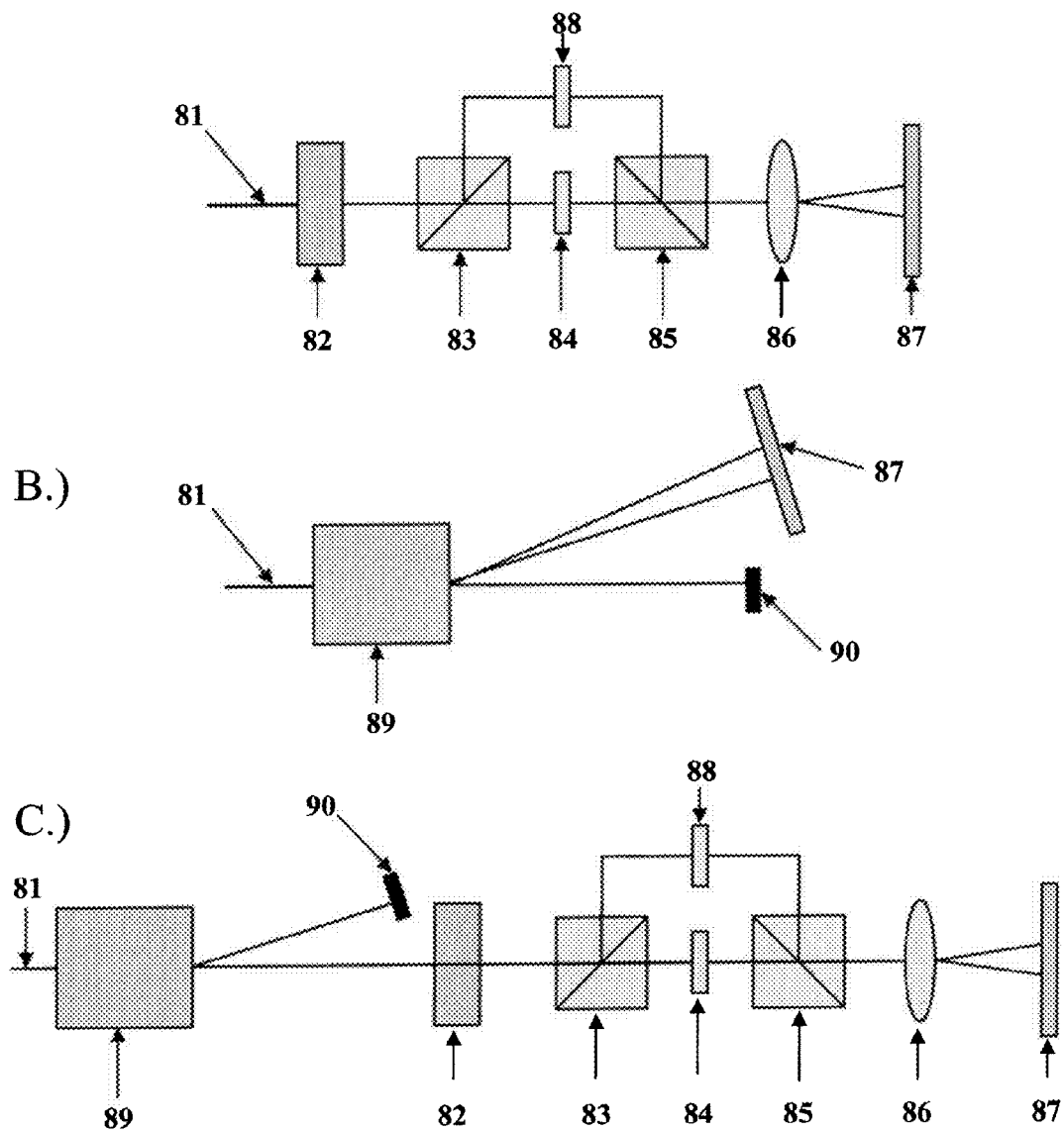

FIG. 8 shows possible optical designs for modulation and/or shuttering of the optical switch.

Figure 9A:
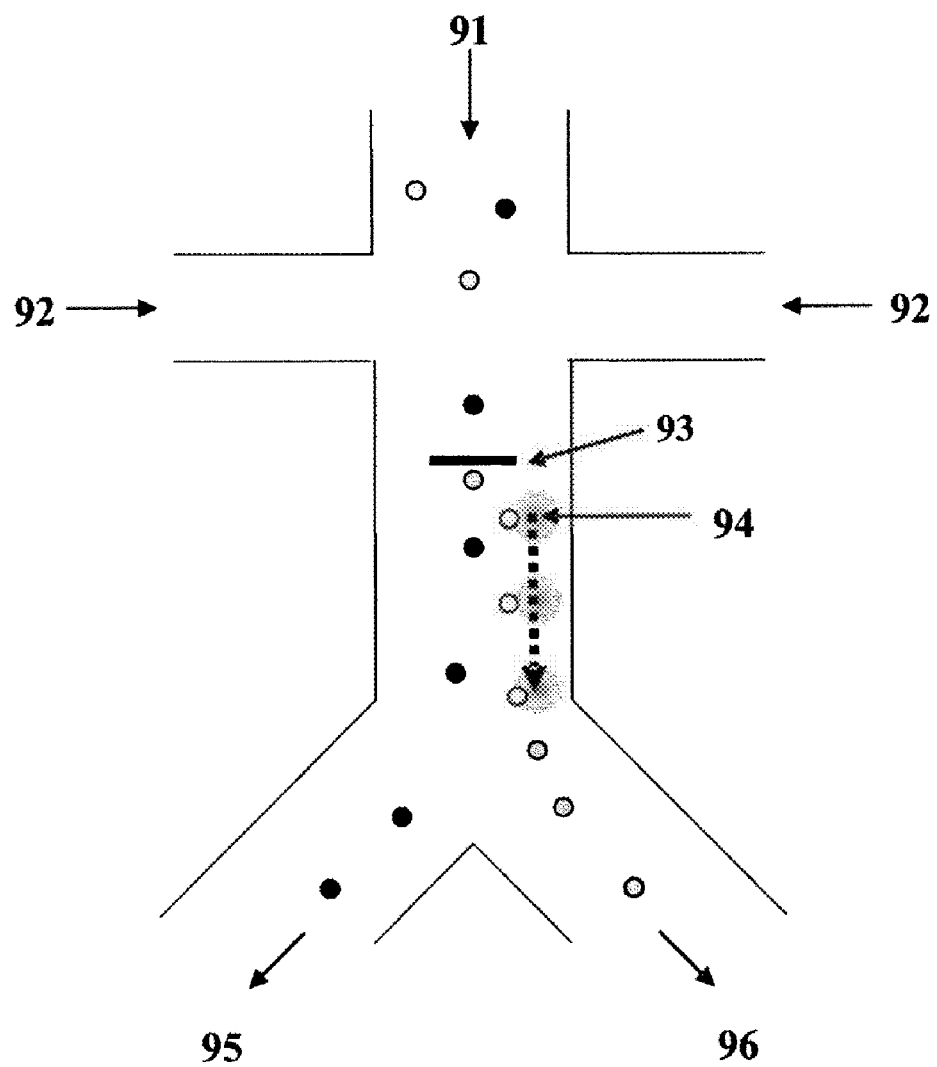

FIG. 9 is a plan view of a sheath flow skewed optical switch network with a laser spot optical switch that is translated parallel to the cell flow or at an angle to the cell flow.

FIG. 10 shows a detector arrangement and timing/trigger diagram using a single laser source for the cell detection and trigger decision method.

FIG. 11 shows a detector arrangement and timing/trigger diagram using two laser sources for the cell detection and trigger decision method.

Figure 12:
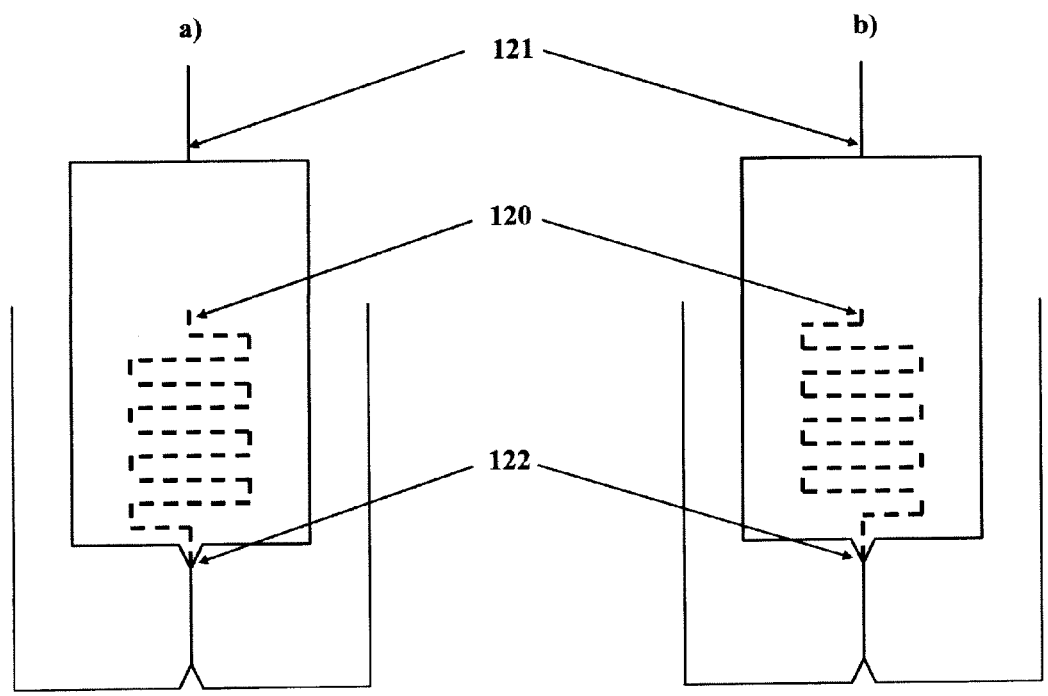

FIG. 12 is a schematic of a representative design for photolithography masks for microfluidic channel networks in both bottom and top glass substrates that provides a 2-dimensional sheath flow pinch of the cell flow in the main channel when these substrates are bonded to form a single network.

Figure 13:
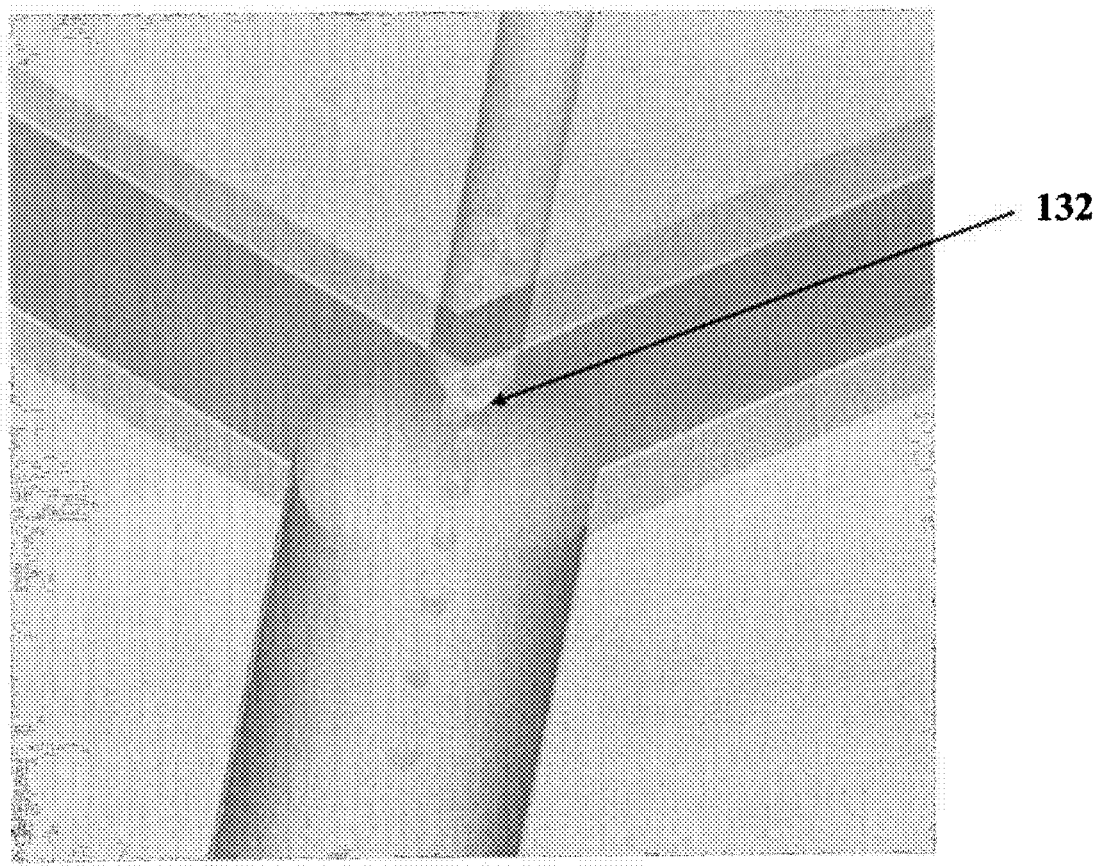

FIG. 13 shows a 3-dimensional illustration of the design described in FIG. 12.

Figure 14:
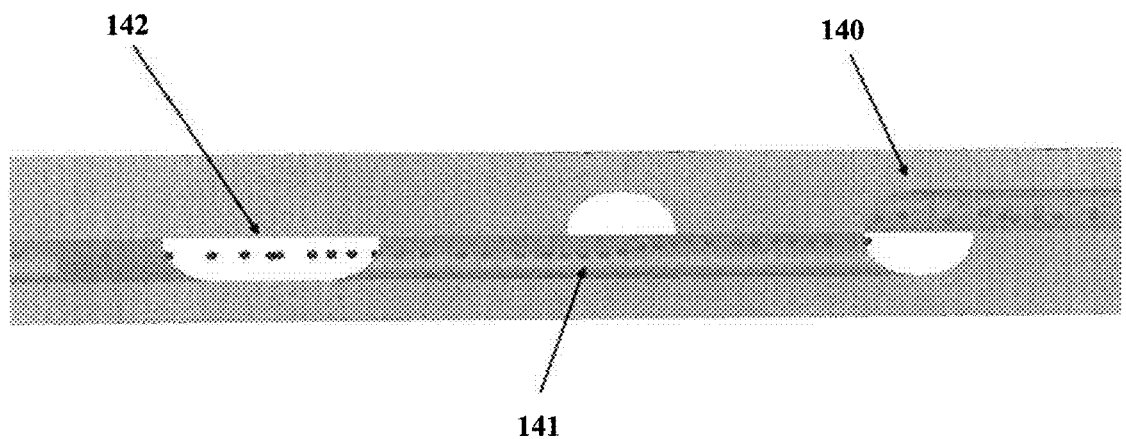

FIG. 14 is an illustration of the side view of a microfluidic channel network that provides sequential sheath flow pinch of the cell flow in the vertical direction and then in the horizontal direction, resulting in full 2-dimensional sheath flow pinch of the cell flow in the main channel.

Figure 15:
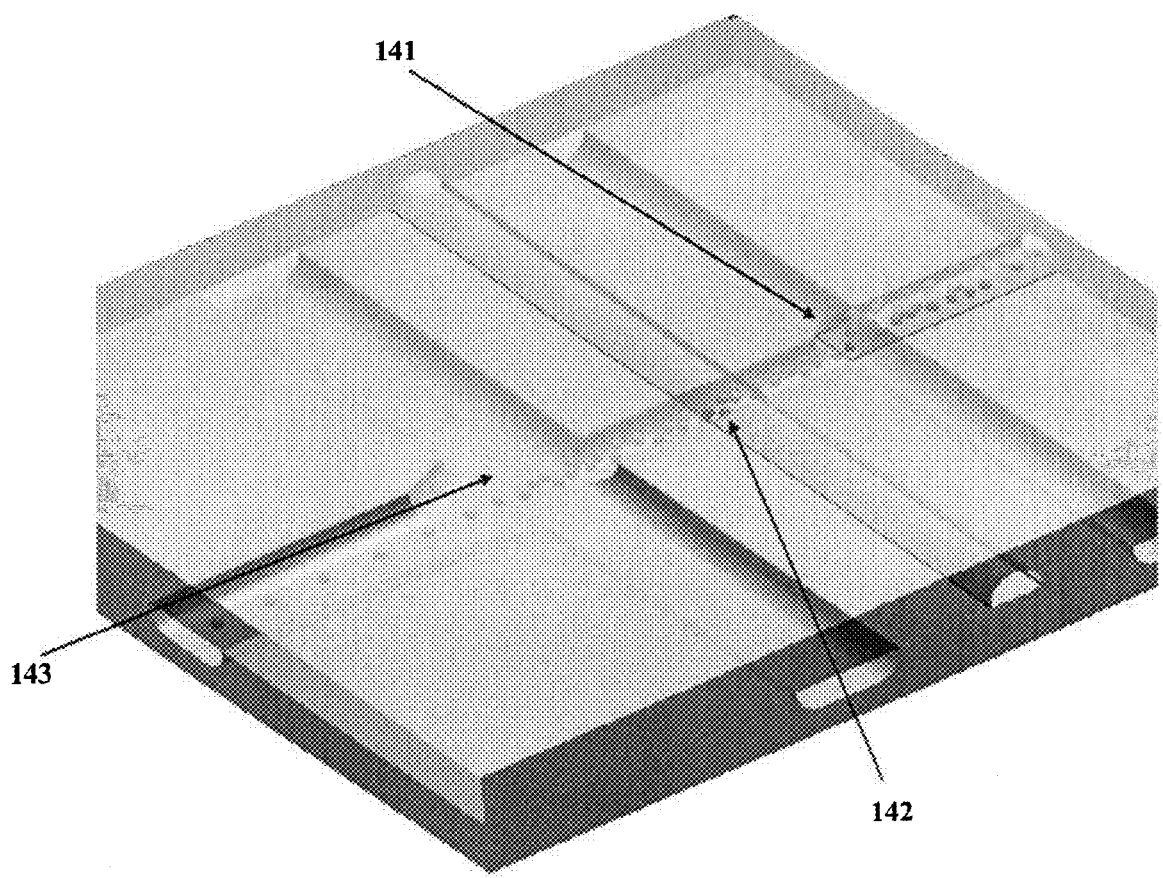

FIG. 15 is a 3-dimensional illustration of the microfluidic channel network described in FIG. 14.

Figure 16:
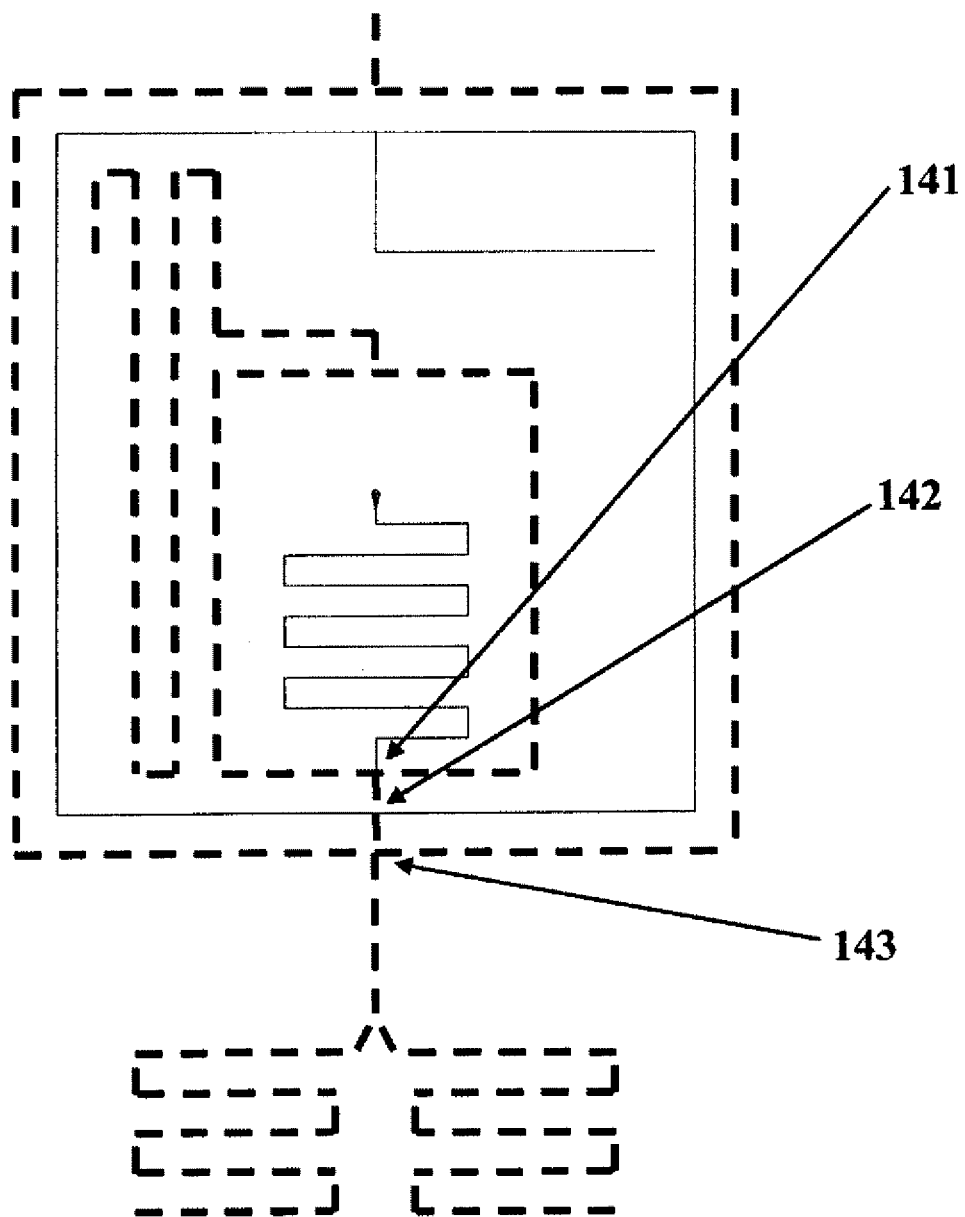

FIG. 16 is a schematic of a representative photolithography mask design for both bottom and top glass substrates that when bonded together form the microfluidic channel network illustrated in FIGS. 14 and 15.

Figure 17:
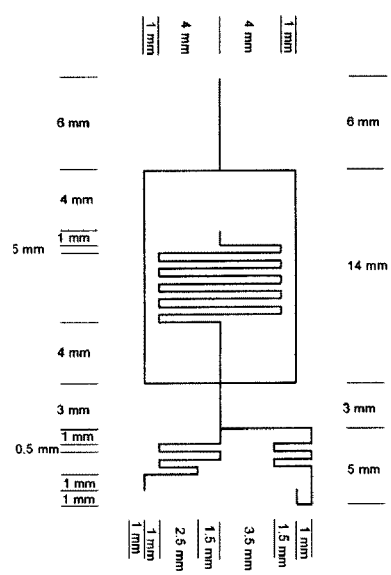

FIG. 17 is a representative embodiment of a photolithography mask for a complete microfluidic channel network, with a T-pinch junction and a T-bifurcation junction to the outlet channels, to implement the optical switch based cell sort method.

Figure 18:
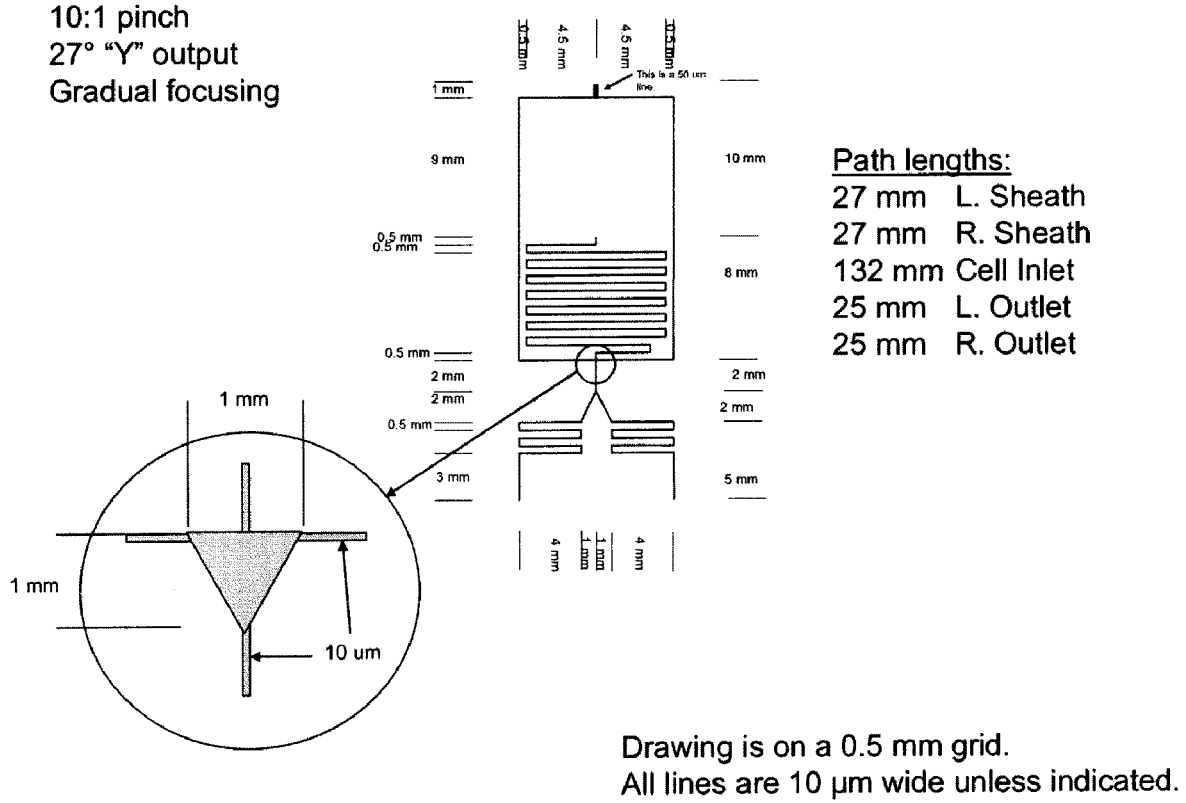

FIG. 18 is a representative embodiment of a photolithography mask for a complete microfluidic channel network, with a triangle-pinch junction and a Y-bifurcation junction to the outlet channels, to implement the optical switch based cell sort method.

Figure 19:
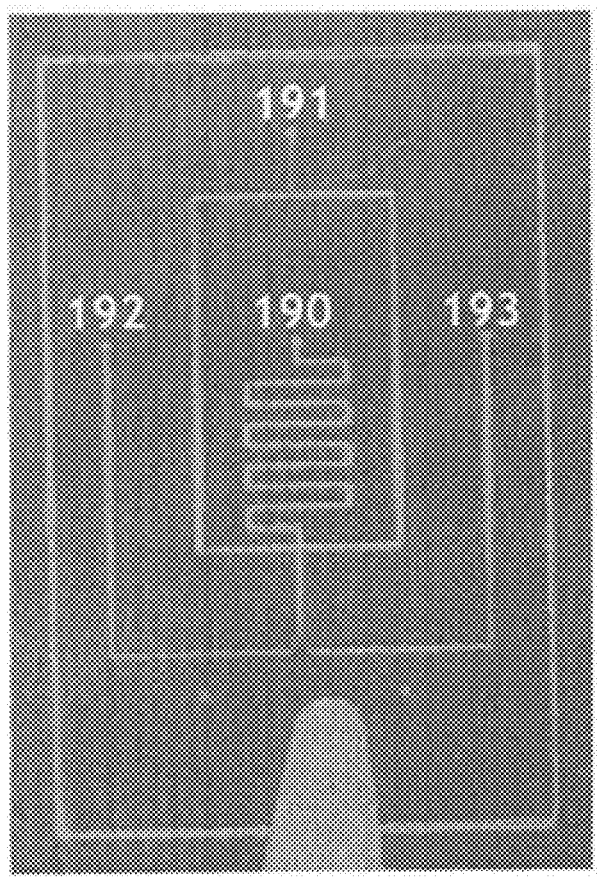

FIG. 19 shows a preferred embodiment of a microfluidic channel network in a completed microfluidic cell sorting chip.

Figure 20:
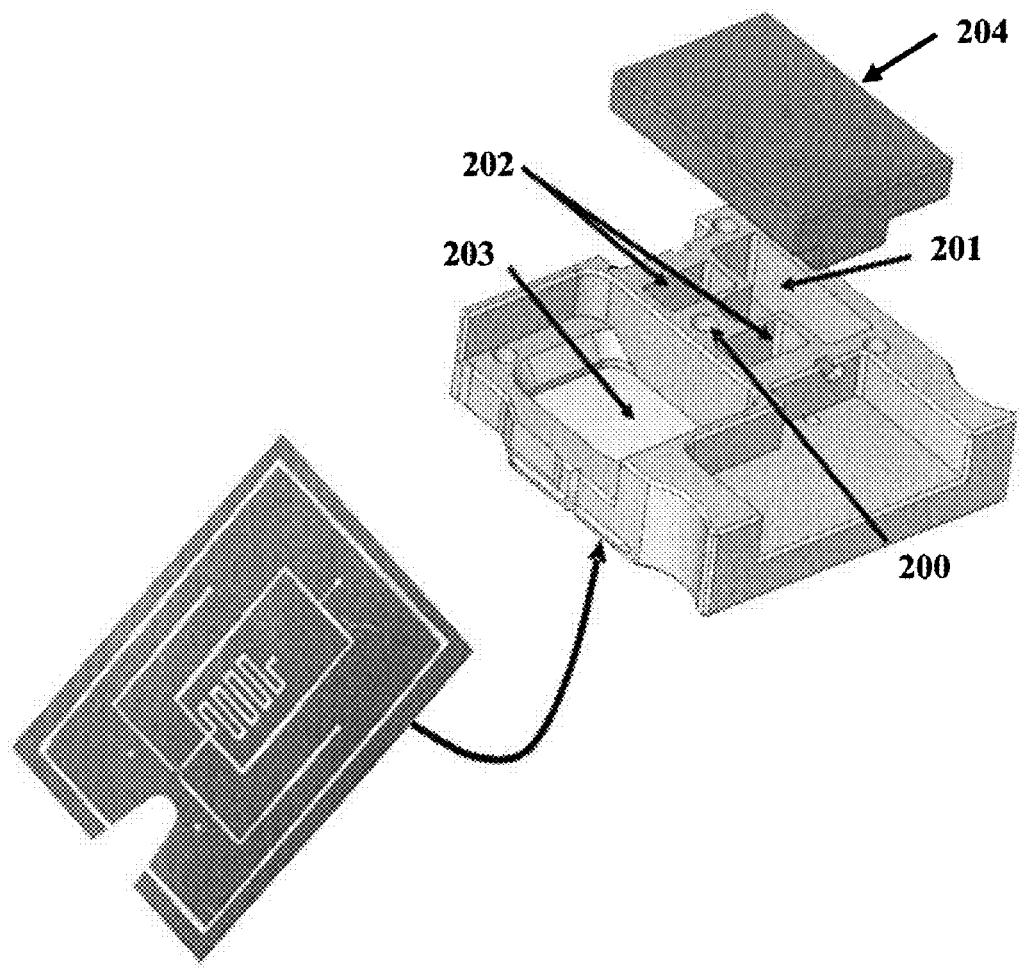

FIG. 20 shows a preferred embodiment for a self-contained disposable cartridge for the optical switch based microfluidic channel network cell sorter.

Figure 21:
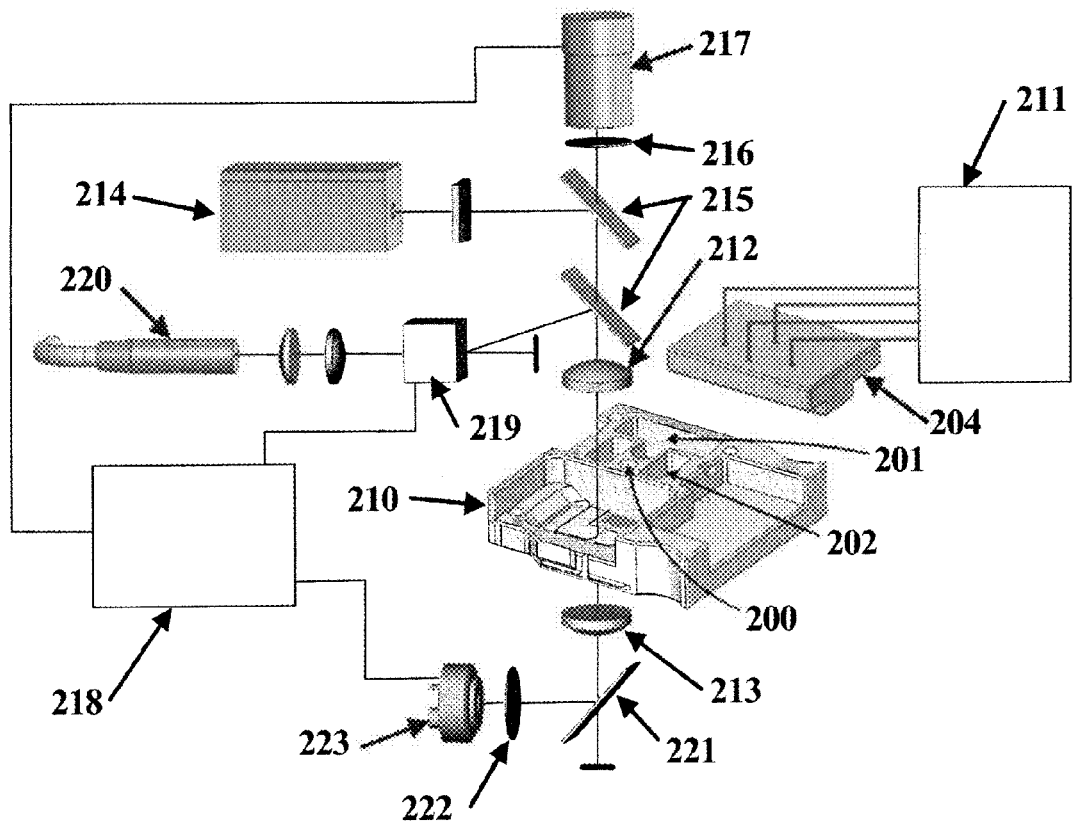

FIG. 21 shows a preferred embodiment of the optical system for the optical switch based microfluidic channel network cell sorter.

Figure 22:
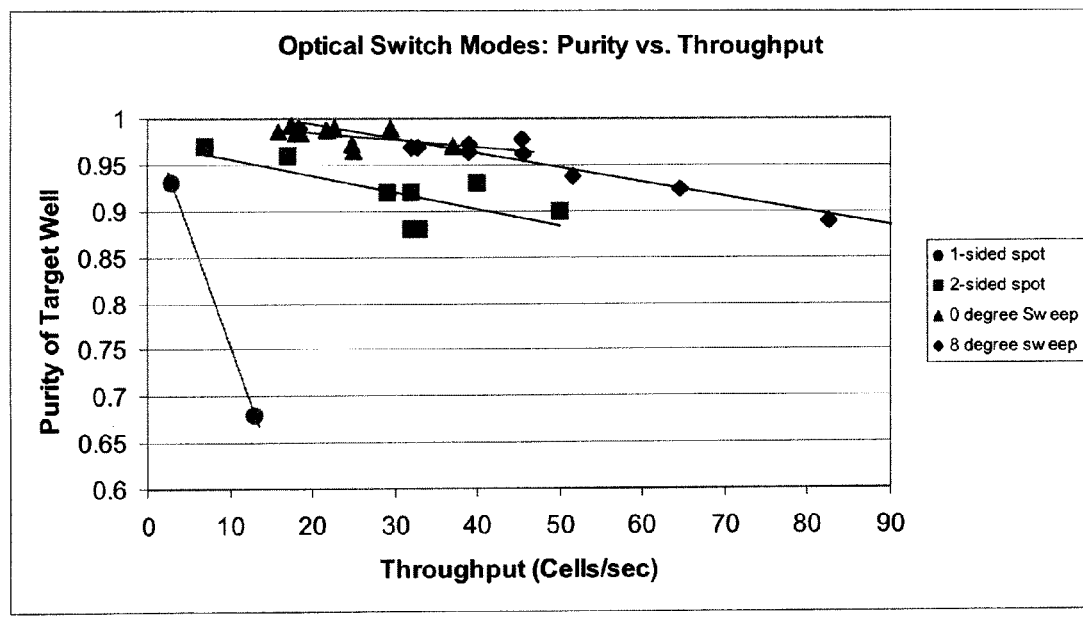

FIG. 22 shows representative performance of the optical switch based microfluidic channel network cell sorter for various implementations of the optical switch.

DETAILED DESCRIPTION OF THE INVENTION

Figure 1:
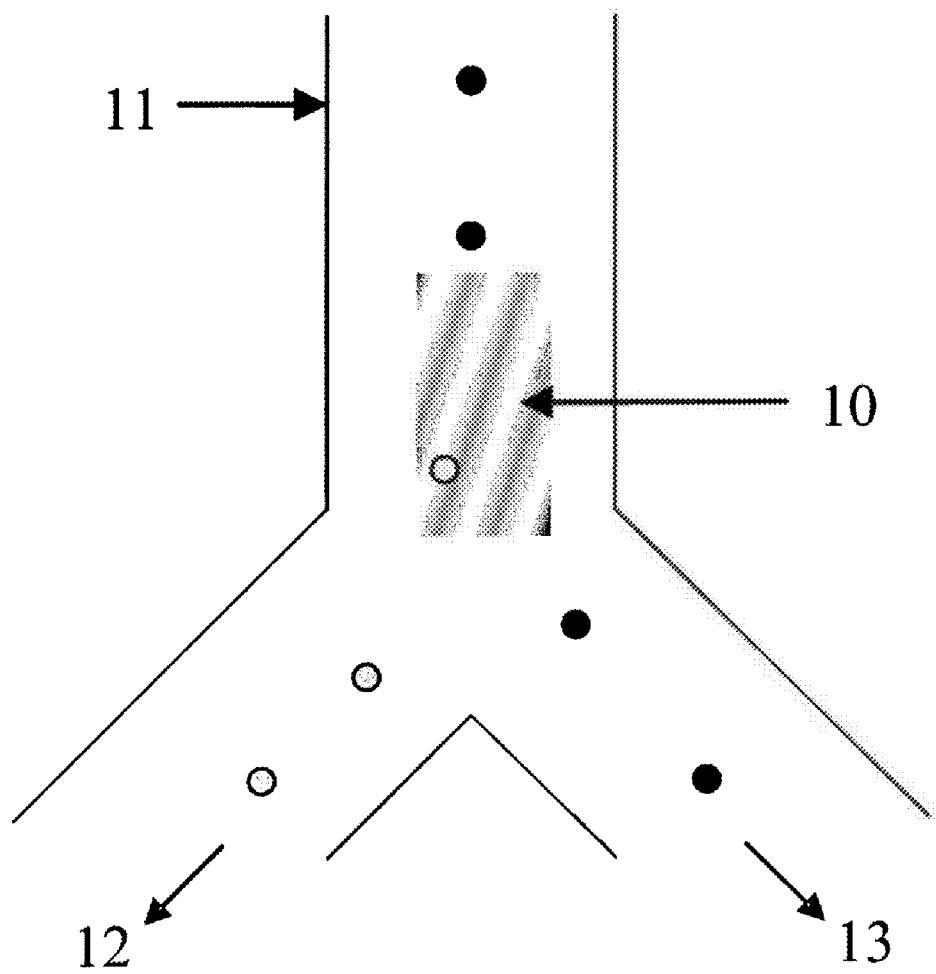
FIG. 1 is a plan view of a "Y" shaped sorting junction in a microfluidic channel network.

FIG. 1 shows one embodiment of an optical switch 10 that serves to sort cells in a 1×2 microfluidic channel network, i.e. a network with one main input channel 11 and two output channels 12 and 13 extending from a bifurcation junction. A "Y" geometry for the bifurcation junction is shown in FIG. 1, but other bifurcations such as a "T" geometry may also be used. In general these microfluidic channels are produced in optically transparent substrates to enable projection of the optical switch and other cell detection optics into the channel. This substrate is typically, but not limited to, glass, quartz, plastics, e.g., polymethylmethacrylate (PMMA), etc., and other castable or workable polymers (e.g. polydimethylsiloxane, PDMS or SU8). The depth of the microfluidic channels is typically in, but not limited to, the range 10 µm to 100 µm. The width of the microfluidic channels is typically, but not limited to, 1 to 5 times the depth. The cross section is typically rectangular, or rectangular with quarter-round corners in the case of microfluidic channels produced by photolithograpic masking of glass substrate followed by isotropic etching of the channels.

The flow conditions are set such that when the optical beam, in this case from a laser, is turned off or blocked so that the beam does not impinge on the junction region, all cells will preferentially flow into one of the output channels, for example the right output channel 13. When the optical beam is turned on or unblocked, the beam strikes the junction region and optical forces generated by the interaction of the cells with the optical beam direct the cells into the left output channel 12. In this example, the optical pattern chosen for directing the cells is a long, thin line of laser illumination at some angle relative to the direction of fluid flow. Optical gradient forces displace the cells laterally, away from the main stream line of cells, such that switched cells then exit the main channel into one output channel, for example 12 while unswitched cells from the main stream of cells exit into the other output channel, for example 13. The setting and control of the flow conditions in the microfluidic channel network can be achieved by direct drive pumping, pneumatic pumping, electro-kinetics, capillary action, gravity, or other means to generate fluidic flow.

The performance of the sorting mechanism in terms of throughput (the temporal rate of cells entering the sorting region at the top of the bifurcation junction), yield efficiency (the fraction of target cells in the target output channel, 12), and purity (the ratio of the number of target cells to the total number of cells in the target output channel, 12), are impacted by various factors, each of which affects the implementation of the optical switch. The optical switch can be characterized by several parameters such as the shape of the optical pattern projected into the sorting junction region of the microfluidic channel network, the position of the pattern with respect to the bifurcation junction, any motion of the optical pattern with respect to its initial position and shape, the duration of activation of the optical switch, the wavelength and power of the laser source used to produce the optical switch pattern, etc. The selection of particular values of these parameters for the optical switch is a critical function of, among other things, the topology and geometry of the microfluidic channel system, the flow rates (cell velocities) within the microchannel system, the ability to control the position of cells flowing in the main channel (whether they are flowing in the center of the main channel or off-set to one side), the amount of displacement of the cells necessary to achieve reliable switching, the depth of the channels, the shape of the channels, and the forces produced by the cells' interactions with the optical switch.

In general, when cells are introduced into the flow in the main channel they may move down the channel at any transverse position within the flow. Consequently the cells may be moving at differing velocities, depending upon their transverse positions due to the well known parabolic (for cylindrical microfluidic channels) or quasi-parabolic (for more general cross sections) velocity profile of pressure driven flow in microfluidic channels. This would make it difficult to bias the flow of all cells to one output channel, say 13, as shown in FIG. 1. Any implementation of an optical switch with this flow geometry would necessarily result in low throughput and inefficient use of the laser power available to produce the optical switch. The use of appropriate flow conditions can help alleviate these restrictions on the performance of the optical switch.

Figure 2:
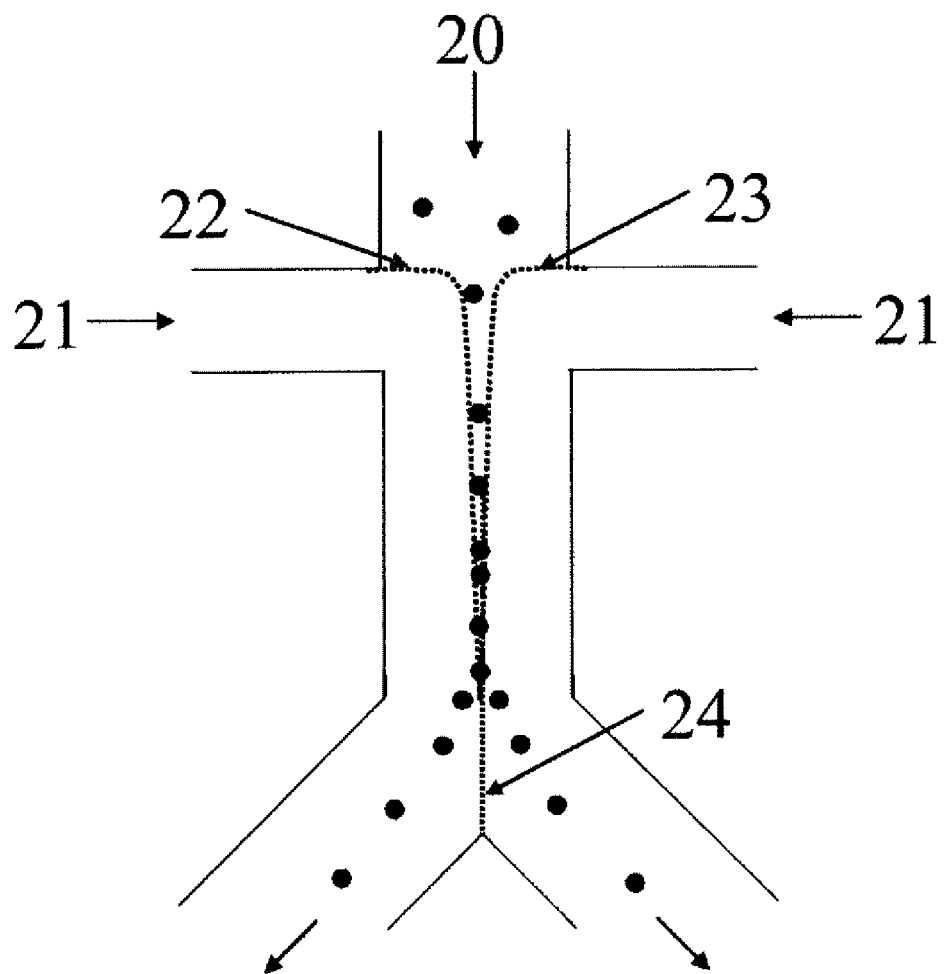
FIG. 2 is a plan view of a microfluidic channel network that incorporates both a sheath flow pinch junction and a "Y" shaped sorting junction connected by a main channel, with 50/50 splitting of cells in the flow, collectively referred to as a 50/50 optical switch network.

Establishing the appropriate flow conditions can be done in many ways. In one embodiment, 1-dimensional focusing of cells (horizontally in the planar view shown) into a single file in the center of the main channel is achieved by pinching the cell input channel flow 20 with added flow of buffer 21 from both the left 22 and right 23 sides, using a sheath flow approach as shown in FIG. 2. Maintaining the cells in the center of the main channel is achieved by having equal flow 21 from each side. This flow effectively creates a fluidic splitting plane 24, as shown in FIG. 2, and this ultimately will result in a 50/50 splitting of the fluid and cells at the bifurcation junction. Implementation of an optical switch to sort target cells from a mixed population of cells using this microfluidic channel design and flow conditions requires an optical switch that actively switches both target cells to one output channel, say 12 as shown in FIG. 1 and non-target cells to the other output channel, say 13.

Figure 3A:
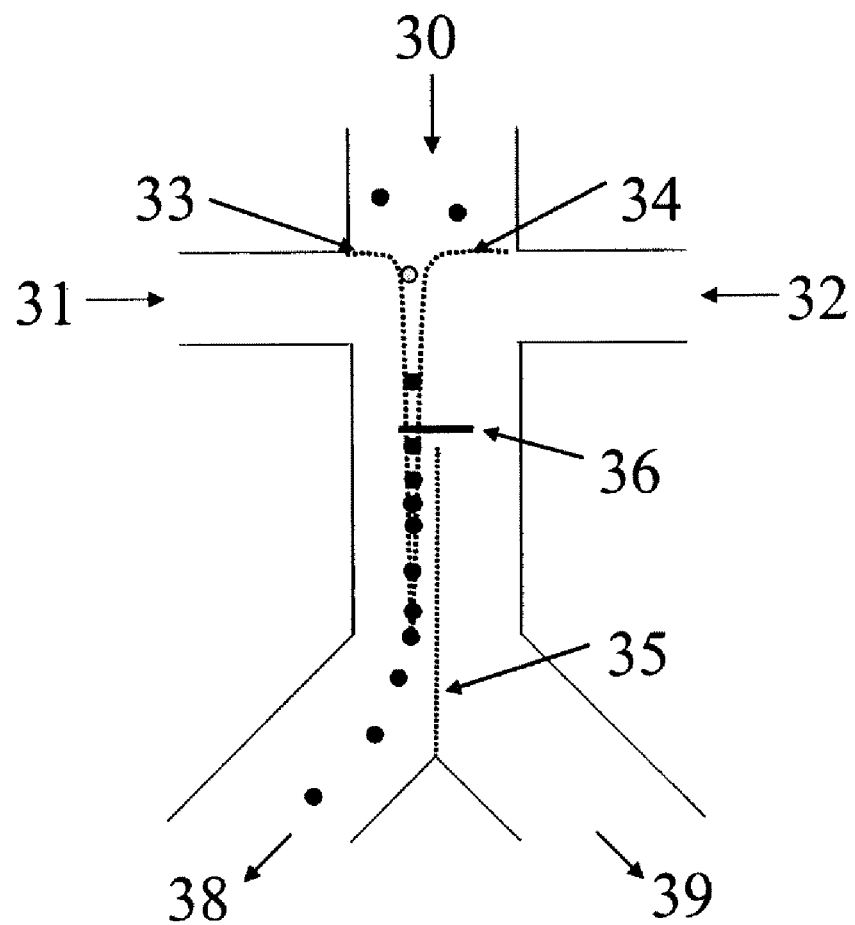
FIG. 3 is a plan view of a microfluidic channel network that incorporates both a sheath flow pinch junction and a "Y" shaped sorting junction connected by a main channel, with skewed splitting of cells in the flow via differential sheath flow, collectively referred to as a sheath flow skewed optical switch network, with an optical switch.
Figure 3B:
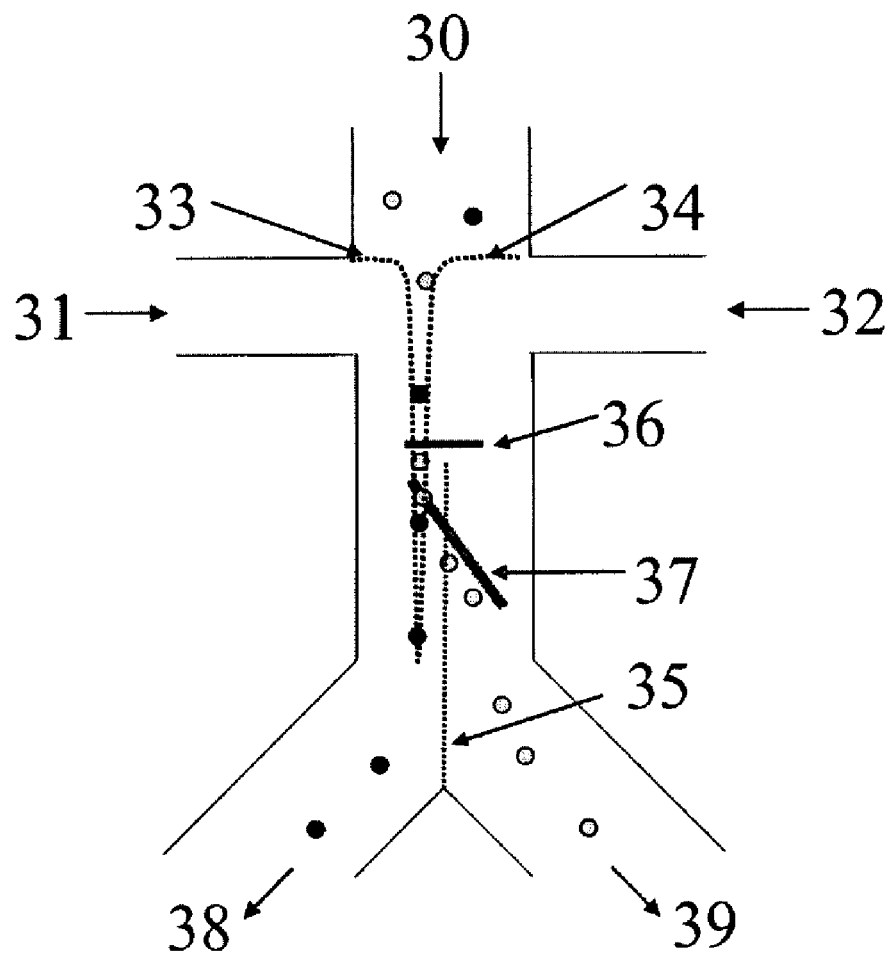
Figure 4A:
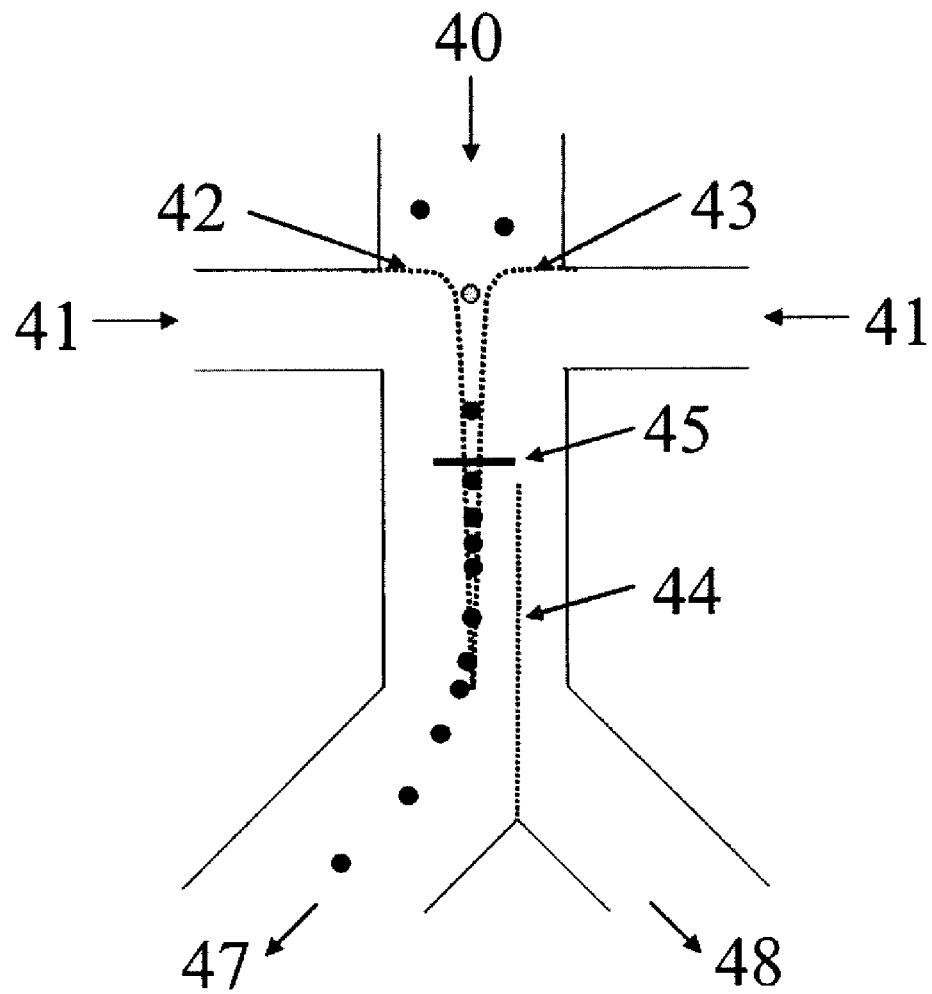
FIG. 4 is a plan view of a microfluidic channel network that incorporates both a sheath flow pinch junction and a "Y" shaped sorting junction connected by a main channel, with skewed splitting of cells in the flow via differential outlet channel width, collectively referred to as an outlet flow skewed optical switch network, with an optical switch.
Figure 4B:
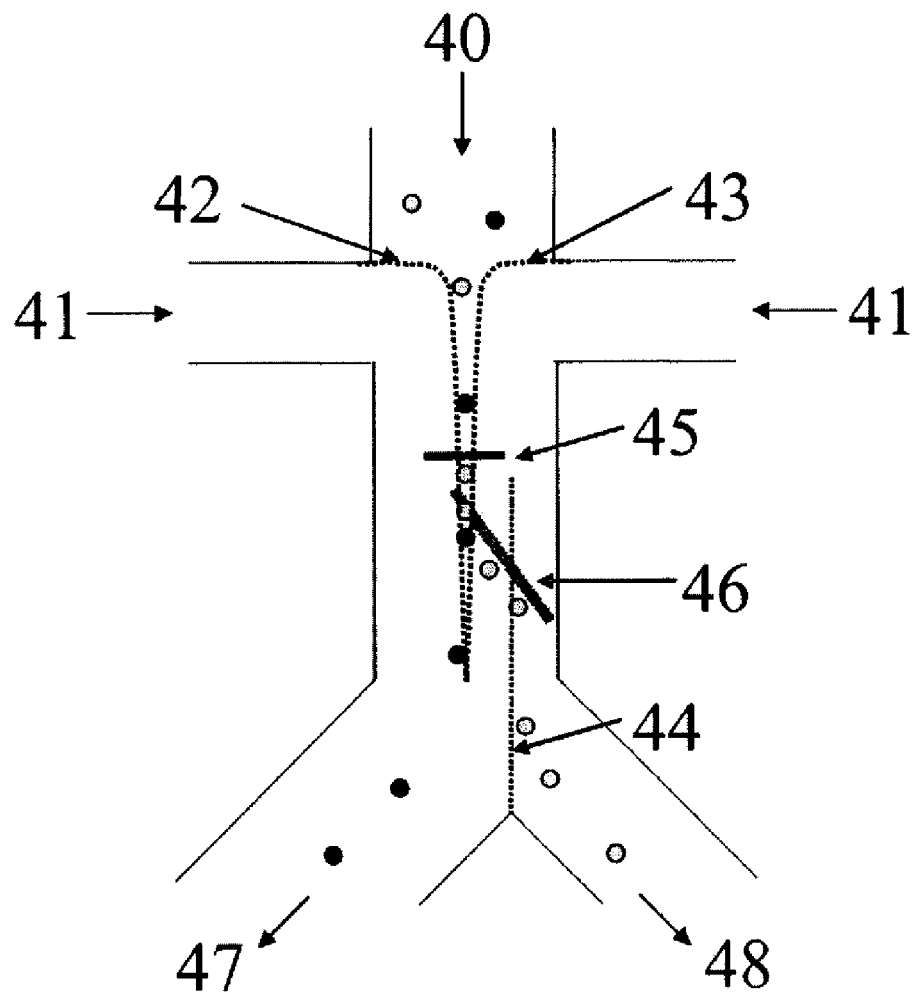

Alternatively, the focused line of cells can be positioned off-set from the center of the main channel by putting unequal flows into the side sheath flow channels, FIG. 3*a-b*. This effectively causes a skewed flow of cells from the input channel 30 to one side of the splitting plane 33 within the main channel. The side of the main channel to which the cell flow is skewed will be opposite to the side in which the sheath flow has the higher flow rate. That is, when the right sheath buffer 32 flows faster than the left sheath buffer 31, the pinch from the right 34 is greater than the pinch from the left 33 and the line of cells is skewed toward the left of the flow in the main channel, as shown in FIG. 3*a-b*. However, the left sheath flow could also have the higher flow which would push the line of cells toward the right side of the main channel. Also shown in FIG. 3*a-b* are a fluorescence detector 36 and an optical switch 37. The fluorescence detector is used as a means to decide which cells to sort, and will be discussed in further detail later. It is evident from FIG. 3*b* that an effective sort involves moving a cell across the splitting plane from a flow stream that exits the bifurcation junction to the fluorescence-negative non-target cell microfluidic channel 38 into a flow stream that exits the bifurcation junction to the fluorescence-positive, target cell microfluidic channel 39. Manipulation of the sheath buffer flow rate can be achieved either by separately controlling the flow rate in the respective side channels using direct drive pumping, pneumatic pumping, electro-kinetics, capillary action, gravity, or other means to generate fluidic flow, or by specifically designing the microfluidic sheath network to ensure that central flow (50/50 splitting) or off-set flow occurs, through careful balancing of the pressure drops in each of the microfluidic channels.

An alternative approach to achieve the preferential flow of all cells from the input flow 40 in the main channel into one output microfluidic channel, say the fluorescence-negative channel 47, prior to fluorescence detection 45, is to obtain central pinching using equal sheath buffer 41 flow rates 42 and 43, but then preferentially bias the cell flow into fluorescence-negative channel by having a larger volumetric fluid flow out of the bifurcation junction into the fluorescence-negative output channel 47 relative to the fluorescence-positive output channel 48. This is demonstrated in FIG. 4*a-b*, in which the left output channel 47 is wider than the right output channel 48. This configuration effectively places the splitting plane 44 to the right of the centrally located cell stream. Therefore, with the cells in the desired position, the optical switch 46 is then used to translate the target cells across the splitting plane into the target cell, fluorescence-positive, right output channel when the fluorescence positive cell is detected at 45. This approach is equally effective by having the right output channel wider than the left output channel, whereby target cells are translated by the optical switch across the splitting plane, which is now located to the left of the centrally located cell stream, and are consequently sorted into the left output channel. Thus, by specifically designing the microfluidic channel outlet network, or by actively controlling the outlet back pressure in the respective outlet channels, the flow of cells into a desired output channel can be controlled.

The use of either central flow or an off-set flow, and the respective distance of the focused cell flow from a fluidic splitting plane, ultimately dictates the magnitude of the displacement of the cells necessary to achieve reliable switching. This further dictates the length of the laser line and the laser power required to achieve reliable switching. The closer the cell stream is to the splitting plane, the shorter the displacement required, and the more efficient the sorting process becomes. For enhanced purity of the sorted population and for high throughput, the single optical switch in a mono-directional arrangement requires the sample stream be offset from the splitting plane. In this manner the occurrence of a mistaken sort is minimized.

An alternative to this design is to use a bi-directional optical switch which utilizes two laser lines. With this approach one laser line sorts the desired cells to one output channel, and the other laser line sorts all other cells into the other output channel. This approach can be used with either the 50/50, FIG. 2, or the offset, FIGS. 3 and 4, splitting configuration. In the latter case when a cell is not in the switching zone, one may choose to leave the laser on in either of its two positional states, or one may also shutter the laser during this time. The optical switch can also be made bi-directional by having two mirror-image laser lines impinging on the switching region, located just above the bifurcation junction, which independently turn on to direct cells to either of the two outputs stemming from the bifurcation junction.

A schematic of the bi-directional optical switch using laser lines in a 1×2 microfluidic network is shown in FIG. 5. As before, all cells from the input flow 50 are pinched to a focused flow by sheath buffer 51 flow from each side. When a fluorescent cell is detected at 52, the line-shaped optical switch 53 is triggered and the cell is switched left to flow into the fluorescence positive target cell channel 55. When no fluorescence is detected at 52, the line-shaped optical switch 54 directs the cells to the right into the fluorescence negative non-target cell channel 56. A similar bi-directional optical switch has also been achieved with laser spots directed to either side of the channel, as shown in FIG. 6. Again, all cells from the input flow 60 are pinched to a focused flow by sheath buffer 61 flow from each side. When a fluorescent cell is detected at 62, the spot-shaped optical switch 63 is triggered and the cell is switched left to flow into the fluorescence positive target cell channel 65. When no fluorescence is detected at 62, the spot-shaped optical switch 64 directs the cells to the right into the fluorescence negative non-target cell channel 66. As with the mono-directional optical switch, a single laser source can be used in the bi-directional optical switch, or alternatively the bi-directional optical switch can use two independent laser sources. The bi-directional design potentially offers some performance advantages versus the mono-directional design. The first is that purity is potentially maximized because every cell is directed by the laser. Secondly, the fluid flow is simplified because equal flow can be directed out each of the two output ports, instead of some predetermined ratio of flow.

Figure 7A:
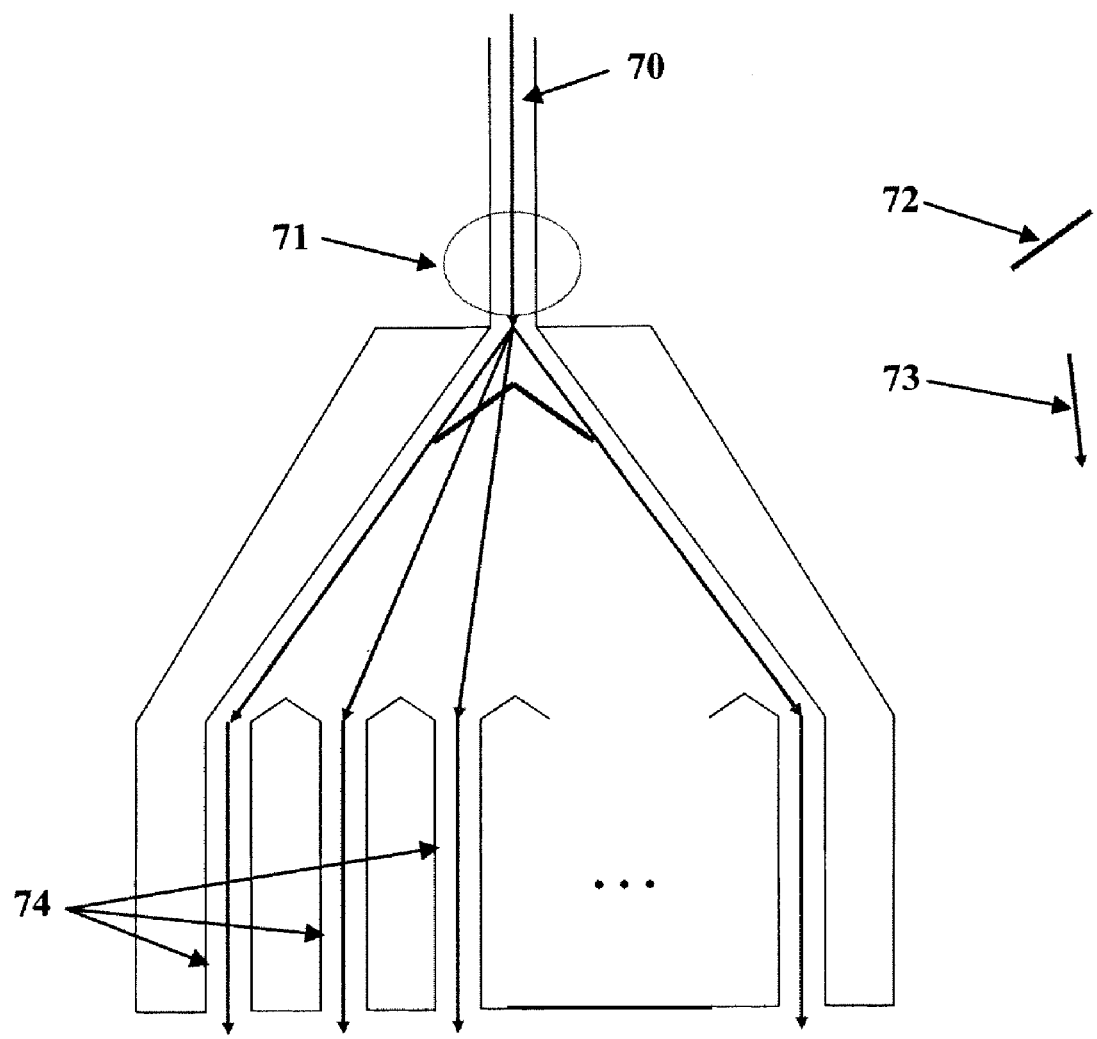
Figure 7B:
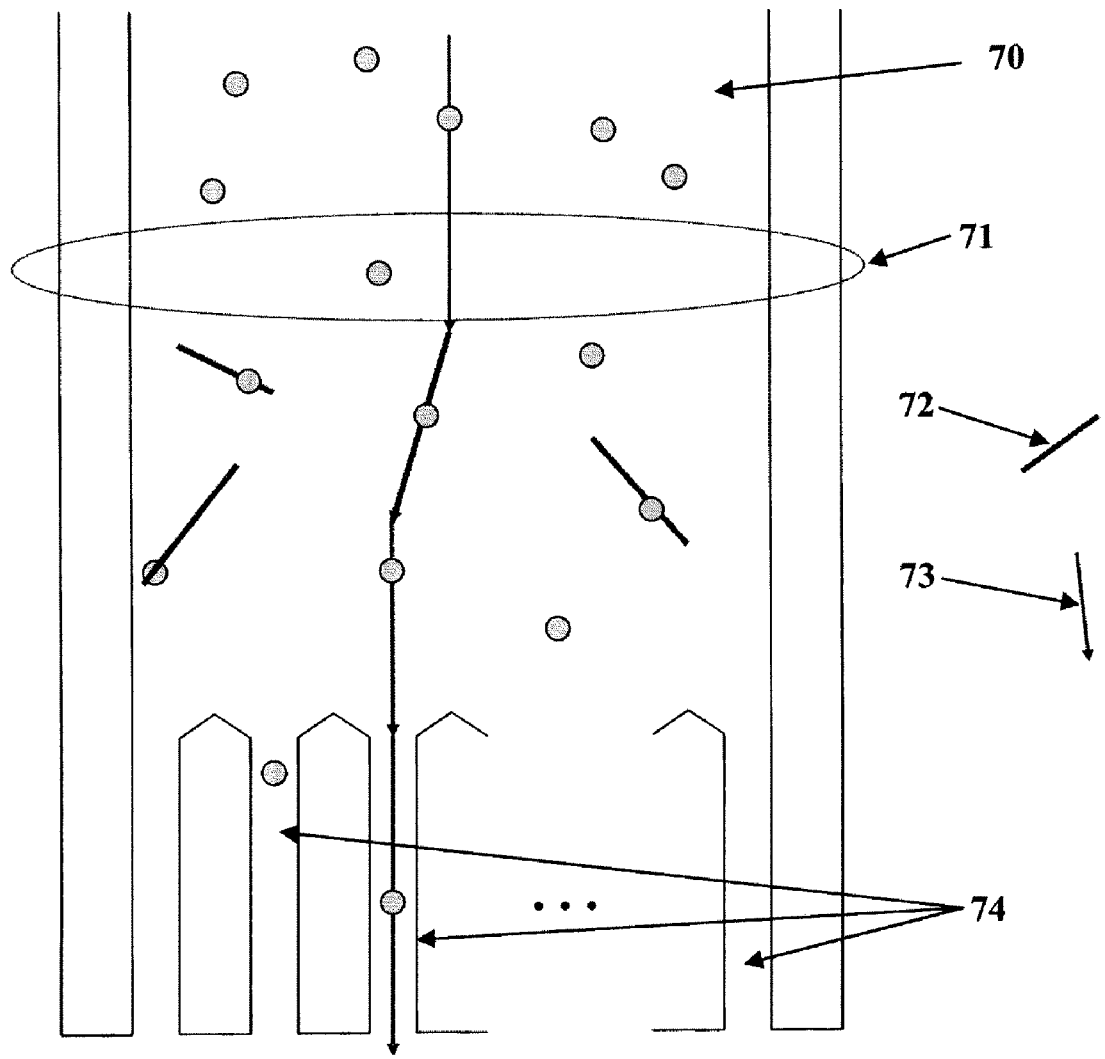
Figure 7C:
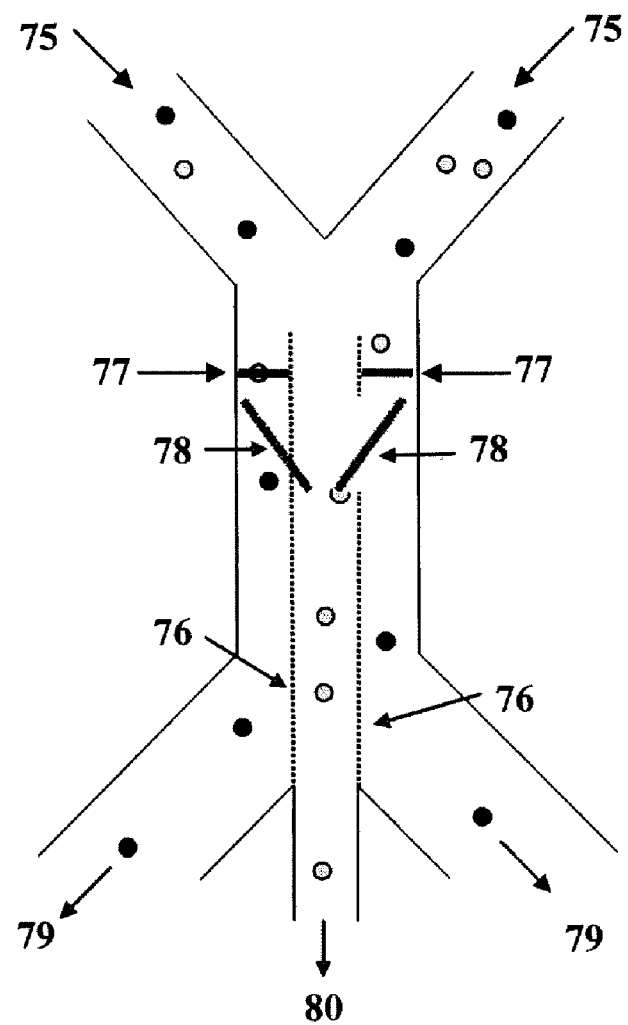

Although only the 1×2 microfluidic channel design with flow through one input main channel into a bifurcation to two output channels has been considered thus far in this description, microfluidic networks with 1×N, or M×N, outputs can be utilized. Optical switching can be achieved in these larger networks by having an arbitrarily large number of independently modulated laser lines. Some embodiments are shown in FIG. 7*a-c*. A possible 1×N fluidic network is shown in FIG. 7*a*, cells flow in enter through focused flow in a single channel 70 and flow through an analysis region 71 where the cell is characterized by measuring properties such as fluorescence and scattering. Based on these measurements, a decision is made to trigger one of multiple possible optical switches 72 to direct the cell to one of multiple possible flow streams 73 that direct the cell to one of multiple possible output channels 74. This concept can be extended to multiple focused clow input channels, resulting in M×N switching instead of 1×N. In FIG. 7*b*, another microfluidic design to achieve 1×N sorting shows cells flowing in a input channel 70 without focused flow. After identification in the analysis region 71 an appropriate target cell can be directed by multiple arbitrarily positioned optical switches 72 to multiple possible flow streams 73 that direct the cells to multiple possible output channels 74. One possible instance of an M×N switching design is shown in FIG. 7*c* as a 2×3 design. In this case there are two cell input flow streams through 2 channels 75 and three output channels, two fluorescence negative outputs 79 and one fluorescence positive output 80. As described above, by proper design of the channel widths, two splitting planes 76 are created in the analysis-sort main channel such that cells flowing between the splitting planes exit the fluorescence positive output channel 80 and cells flowing outside the splitting planes exit through the fluorescence negative output channels 79. Fluorescence detectors 77 distinguish between target and nontarget cells. When a fluorescence positive target cell is detected in one of the input flow streams, the optical switch 78 for that flow stream is triggered and the cell is switched to the fluorescence positive flow stream that is common to both input streams. This and similar M×N microchannel designed can be realized in instances with M greater 2 and N greater than 3. Furthermore, cells can also be fed back multiple times through the same sorter to increase the purity of the sort, or alternatively, channels can also be arranged in a cascade for multiple levels of sorting.

Two different activation modes can be considered when operating the optical switch in a mono-directional or bi-directional arrangement; a passive mode or an active mode. The passive mode is such that the state of the optical switch is either on or off, regardless of what cell may be flowing through the channel. In this case knowledge of when or how many cells are entering the switching region is not required, and consequently, depending on the state of the laser, all cells within the switching region are switched. Alternatively, in the active mode the cells are first detected as they enter a detection/selection region, and then are switched based on some decision process. FIG. 3*a-b* and FIG. 4*a-b* show examples of this mode that use a fluorescence detector placed just prior to the switching region. In this case, all fluorescent cells were directed to one output channel, and all non-fluorescent cells were directed to the other output channel. Other non-fluorescent detection/selection techniques for the decision process include Time-Of-Flight, scatter, imaging, capacitance, or any detection modality that can identify a desired cell. Regardless of the detection/selection method, switching using the active mode can be utilized to sort one population of cells from another based on some decision process.

In order to utilize the active mode, the optical beam must be modulated on or off in response to the decision process. Regardless of the number of lasers used, or whether the optical switch is mono-directional or bi-directional, the lasers can be modulated in many ways, including using an electro-optic modulator, modulating the laser power, shuttering the laser, using a liquid crystal modulator, using a galvanometer, and using an acousto-optic modulator. For the bi-directional optical switch with two lasers, the separate lasers can be turned on and off independently; however, when using a single laser source the two different orientations of the optical switch line can be achieved by using a polarization rotator (such as a liquid crystal modulator) and having each of the two different line patterns be each of two separate polarizations. Similarly, an acoustic-optic modulator or a galvanometer mirror can be used to modulate the position of a single spot used as the optical switch, or a two-axis acousto-optic modulator or two-axis galvanometer mirror can be used to draw two different line shapes to be used as the bi-directional optical switch.

FIG. 8 shows three different possible optical designs for performing the, modulation and/or shuttering of the optical switch. In FIG. 8*a* the bi-directional optical switch is created from a single optical beam (laser) 81 directed toward and passing through a Liquid Crystal Modulator (LCM) 82. The LCM is a polarization rotator and therefore if the beam is polarized in one direction it will pass straight through the Polarizing Beam Splitter (PBS) 83, through a cylindrical lens 84 creating a line shape, through another PBS 85, and then through some focusing optics 86 which focus the line onto the microfluidic switching region 87. This effectively creates one line of the bi-directional optical switch used to switch cells into one of the bifurcated channel outputs. To switch cells into the other output channel a mirror image line must be created. This is accomplished by rotating the LCM 82 which alters the polarization of the beam. Consequently, when the beam strikes the first PBS 83 it is directed into an alternate path through a different cylindrical lens 88 (creating a line shape), through the other PBS 85, which directs the beam back through the focusing optics 86 which focus the mirror image line onto the microfluidic switching region 87. Note that the cylindrical lenses were used to create the line shape for the bi-directional optical switch; alternatively the cylindrical lenses can be removed resulting in spots used for the optical switch. In FIG. 8b, rather than use the combination of the LCM and PBS, with or without the cylindrical lenses, an Acousto-Optic Modulator (AOM) 89 can be used to create the lines or spots used in the bi-directional optical switch. This is achieved by configuring the AOM to obtain the desired line shape that is required. Also, the AOM can be used to shutter the optical beam 81 in an on/off fashion, directing the beam to a beam stop 90 for the Optical Switch off condition. FIG. 8c shows the combination of the systems described in FIG. 8a and FIG. 8b. In any configuration that uses an AOM to vary the direction of the beam, a galvanometer mirror, either one-axis or two-axis, depending on the desired beam motion, may be used in place of the AOM.

Many variations for the optical pattern can be considered when optimizing switching efficiency for mono- or bi-directional optical switches. As mentioned above a laser line has been used as the optical switch pattern. The line might be generated by a cylindrical lens, by scanning a galvanometer mirror or an acousto-optic modulator, by a diffractive optic, by a custom refractive optic, or by any other technique to date the line has been generated using a cylindrical lens, by scanning a galvanometer or by using an acousto-optic modulator. The length of the line can be arbitrarily long or as short as a single point. The line can have higher intensity at the top of the line and gradually taper down in intensity toward the end of the line. Additionally the line might be a curved arc which optimizes the output direction of the cells. Additionally, in real time the angle of the line or the shape of the line might vary (i.e. swivel to optimize output). For implementations with multiple output channels, any arbitrary pattern of lines in 2D space might be generated to optimize the direction of each output cell. Alternatively, the line might be created by an array of discrete spots.

Figure 9B:
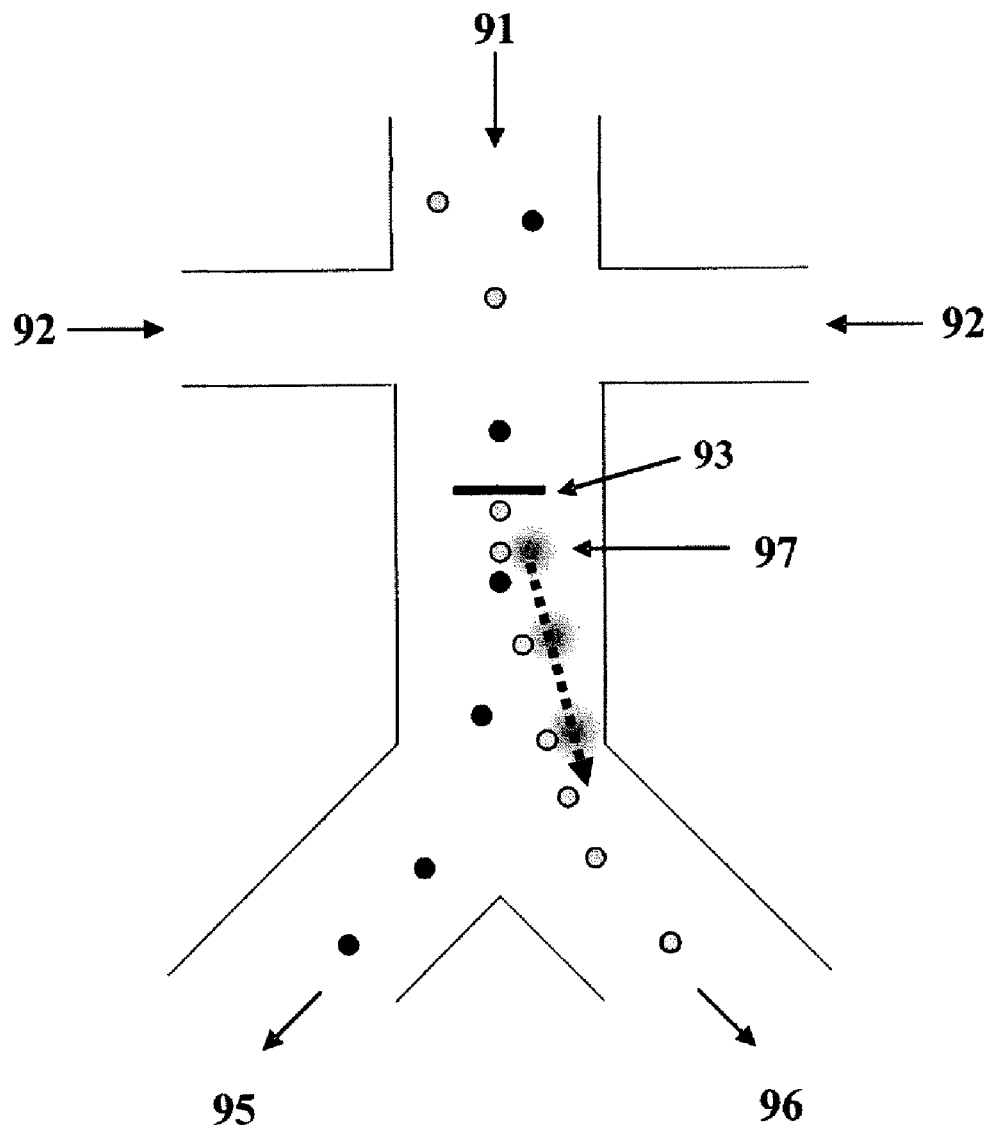

To further improve the performance of the sorting mechanism in terms of throughput, yield efficiency, and purity, the optical switch has been configured such that the laser spot is swept alongside a selected cell as it flows, after 1-dimensional focusing by sheath buffer flow 92, from the input channel 91 down the main channel toward the bifurcation junction, thereby increasing the total interaction time between the cell and the laser. The optical switch utilizes a laser spot which is translated, in a straight line, down the length of the main channel toward the bifurcation junction. The line swept by the spot can be parallel with the walls of the main channel 94 (FIG. 9a), or can be at some angle relative to the cell flow stream 97 (FIG. 9b). Therefore, the angle can range from 0-90 degrees. The ability to sweep the spot is achieved using either an AOM or scanning galvanometer mirrors. The optical switch is triggered to sweep by a decision based on detection of the desired cell using fluorescence or other detection modality that can identify a desired cell 93, for example Time-Of-Flight, scatter, imaging, or capacitance. The cell position can be either off-set or centered in the main channel, which dictates the length of the line swept by the spot and the laser power used to achieve efficient switching/sorting. Thus, as a desired cell is detected the optical switch is turned on, and the spot appears alongside the desired cell. The spot then tracks alongside the selected cell and uses optical forces to direct the selected cell into the desired fluorescence-positive target cell output channel 96; otherwise the cell exits through the fluorescence-negative non-target cell output channel 95.

Two approaches to facilitate efficient triggering of the optical switch are described below. Typical to both methods is the use of a temporal signal to analyze the moving cell, and use this information to generate a decision to switch, or not to switch. This temporal signal is essentially a measure of a signal as a function of time, which can yield a distinctive temporal fingerprint in terms of both peak intensity and peak width. The signal may be fluorescence, scatter (for instance, forward scatter), capacitance, imaging, or any detection modality that can identify a desired cell. One approach is to utilize a single laser source coupled with two or more detectors to accomplish both cell detection and cell identification. FIG. 10a-d show this approach using one laser source combined with a fluorescence detector and a forward scatter detector. The temporal signals from these detectors are used as the information for the switch decision. The presence of a cell is verified by the forward scatter signal and when this signal is coupled with a fluorescence signal intensity which is within a predetermined range; this "gating" information is then used to trigger the optical switch. Note that only a single fluorescence detector is shown, however multiple fluorescence detectors can be used for further refined cell identification. In the case depicted the cell stream is centrally located by using equal flow rate sheath buffers, with non-target 105 and target 106 output channels having different widths used to create a splitting plane to the right of the cell stream. However, any configuration used to manipulate the position of the cell stream and splitting plane, as discussed above, can be used. Also, common to both configurations is the presence of an error checking detector 104 in the target cell output channel, which verifies whether a cell has been switched or not. The detection in this case can be based on fluorescence, scatter (for instance forward scatter), capacitance, imaging, or any detection modality that can identify a desired cell.

Figure 10A:
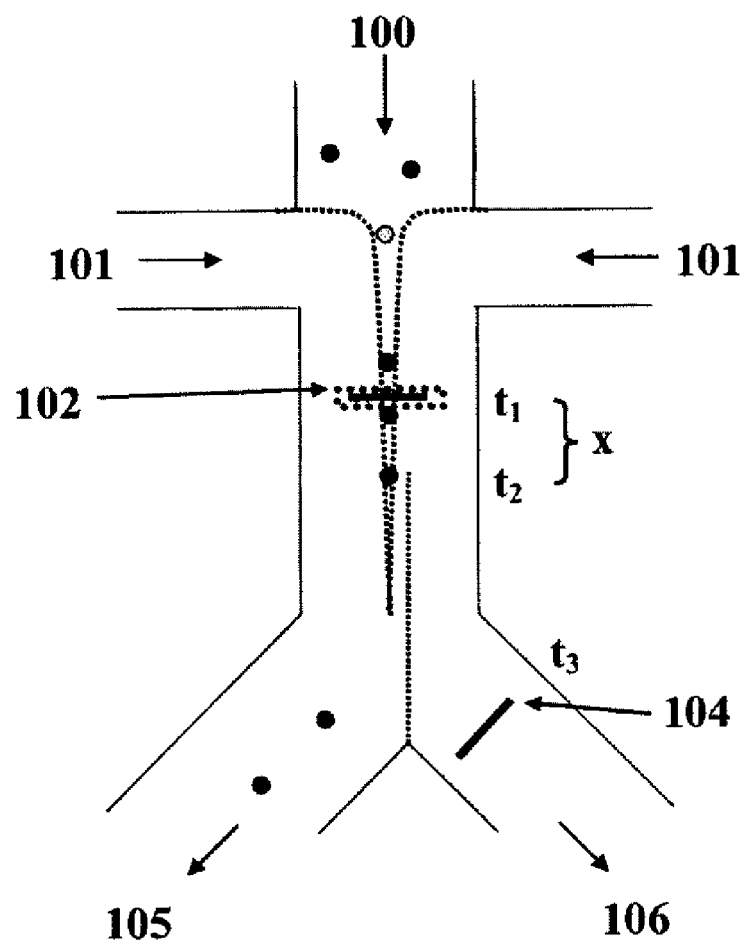
Figure 10B:
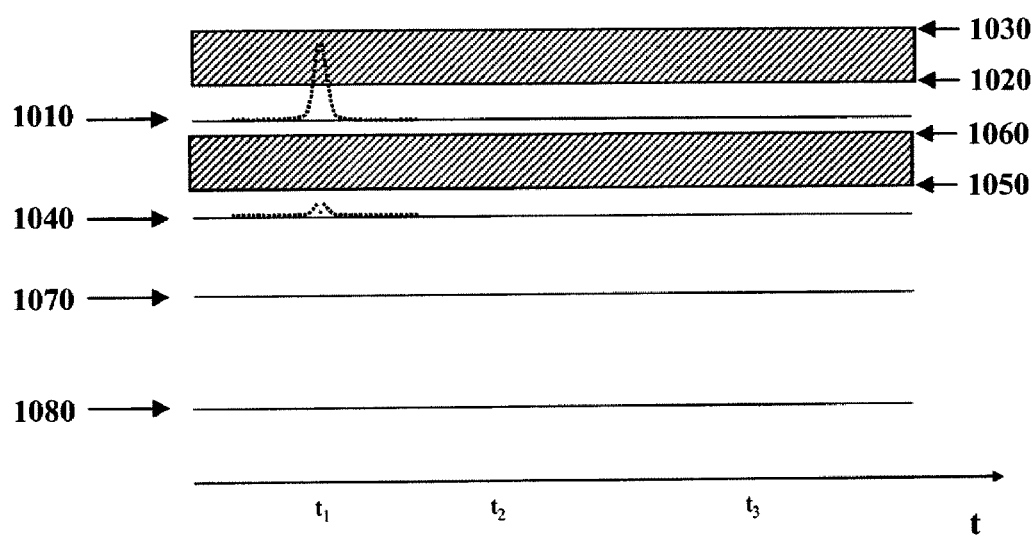
Figure 10C:
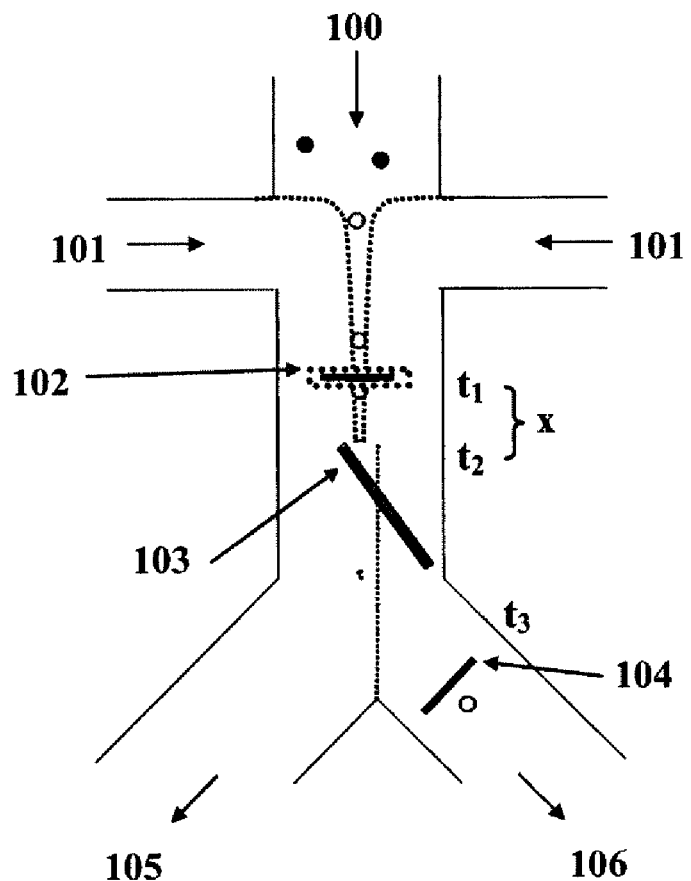
Figure 10D:
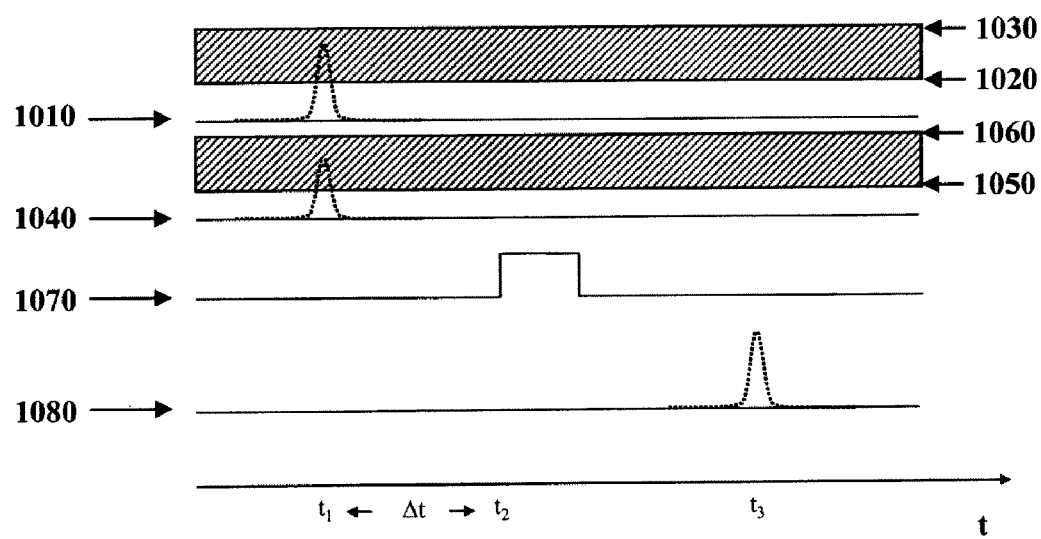

FIG. 10a-b show the detector arrangement and the timing/trigger diagram for when the sort parameter is negative and the optical switch is not triggered. The cells enter the main fluidic channel 100 and are focused into a single file by sheath buffer 101 flowing from both sides. As a cell passes the through the laser in the detection/selection region 102, both fluorescence and forward scatter signals are detected simultaneously, or nearly simultaneously. Although the presence of a cell is successfully detected via the forward scatter signal 1010 which has an amplitude greater than the lower gate limit 1020 and less than the upper gate limit 1030 (at time $t_1$), the fluorescence signal 1040 is below the lower gating level 1050 and the optical switch is not triggered (at time $t_2$). Thus, no error check signal (at time $t_3$) is obtained from the detector 104 since no cell was switched. Alternatively, FIG. 10c-d show the detector arrangement and the timing/trigger diagram for when the sort parameter is positive and the optical switch is triggered. Here, as a cell passes through the laser in the detection/selection region, both fluorescence 1040 and forward scatter 1010 signals are again detected (at time $t_1$) simultaneously, or nearly simultaneously, but the fluorescence signal 1040 is between the gating levels 1050 and 1060 as well as the scatter signal 1010 being between the gating levels 1020 and 1030, and the optical switch is triggered (at time $t_2$). An error check signal 1080 (at time $t_3$) is obtained since a cell was switched. In this approach the trigger time (at time $t_2$) is a preset value $\Delta t$ measured from the initial detection time $t_1$, and this $\Delta t$ value is determined by the speed of the cells and the position of the optical switch relative to the detection/selection region. This approach is satisfactory to achieve efficient sorting; however as a means to further improve the triggering accuracy a second approach is used.

FIG. 11*a-d* shows this second approach, in which two laser sources are used instead of one. Also, as with the single laser approach described above, the temporal signals from these detectors are used as the information for the switch decision. One laser is used in a detection zone 117 to separately accomplish cell detection prior to the identification/selection region. The detection in this case can be based on fluorescence, scatter (for instance forward scatter), capacitance, imaging, or any detection modality that can identify a desired cell. The second laser is coupled with two or more detectors and is used to accomplish cell detection and cell identification 112. Again, identification in this case can be based on fluorescence, scatter (for instance forward scatter), capacitance, imaging, or any detection modality that can identify a desired cell. The purpose for two sequential cell detection steps is such that the cell flow rate can be obtained from the time difference $\Delta t$ between the first detection (at time $t_0$) and the second detection (at time $t_1$). Knowing the spacing between detector windows (d) will yield the flow rate ($v=d/\Delta t$), and this value combined with the known distance the optical switch is from the identification window (x) is then used to calculate the triggering time for the optical switch ($t_2=t_1+x/v$). Again switching only occurs when specific gating levels are reached for the cell identification step. Although only a single fluorescence detector is shown for identification, multiple fluorescence detectors can be used. In the case depicted the cell stream is centrally located by using equal flow rate sheath buffers, with non-target 115 and target 116 output channels having different widths used to create a splitting plane to the right of the cell stream. However, any configuration used to manipulate the position of the cell stream and splitting plane, as discussed above, can be used. Also, common to both configurations is the presence of an error checking detector 114, which verifies whether a cell has been switched or not. The detection in this case can be based on fluorescence, scatter (for instance forward scatter), capacitance, imaging, or any detection modality that can identify a desired cell.

Figure 11A:
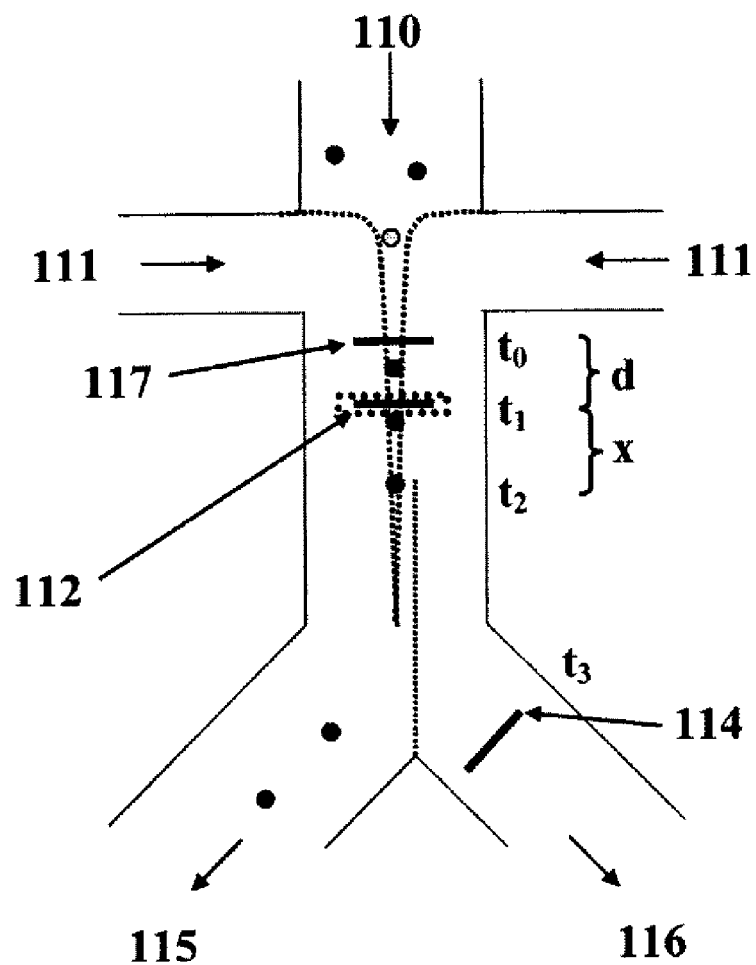
Figure 11B:
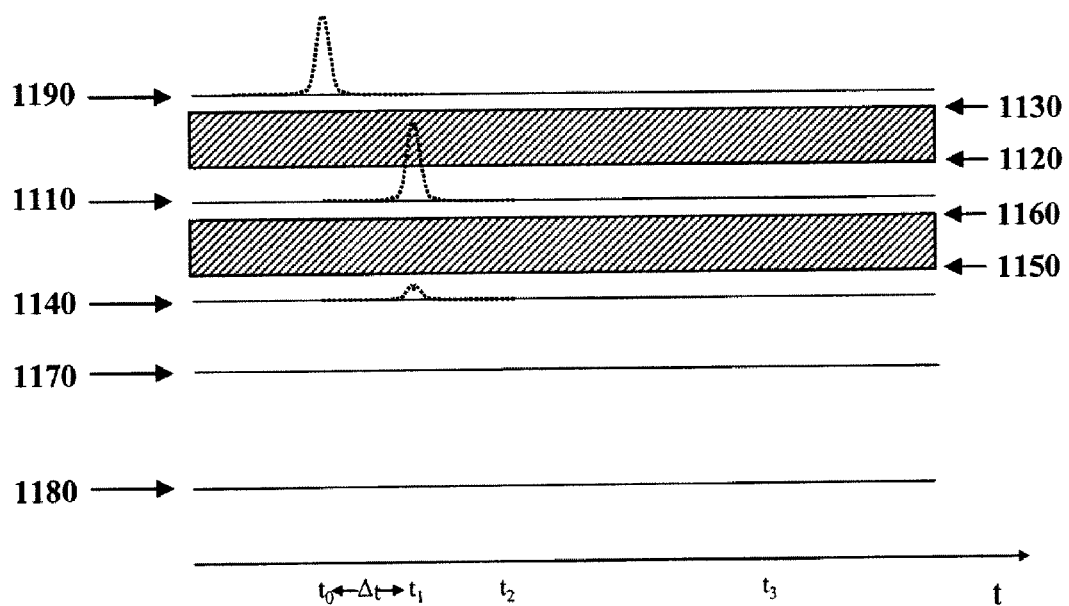

FIG. 11*a-b* shows the detector arrangement and the timing/trigger diagram for when the sort parameter is negative and the optical switch is not triggered. The cells enter the main fluidic channel 110 and are focused into a single file by sheath buffer 111 flowing from both sides. The presence of a cell is verified by the forward scatter signal 1190 (at time $t_0$) as it passes through the detection window region 117. As the cell passes through the identification/selection window 112 a second forward scatter signal 1110 which has an amplitude greater than the lower gate limit 1120 and less than the upper gate limit 1130 is obtained (at time $t_1$), however, this signal is coupled with a fluorescence signal intensity 1140 (at time $t_1$) which is not between the gating levels 1150 and 1160 and the optical switch 1170 is not triggered (at time $t_2$). No error check signal 1180 (at time $t_3$) is obtained since no cell was switched. Even without sorting a cell the flow rate (v) of the cell stream is obtained using ($t_0$), ($t_1$) and the known distance (d) between the detection and identification windows. This is obtained using the relationships: $\Delta t=t_1-t_0$ and $v=d/\Delta t$.

Figure 11C:
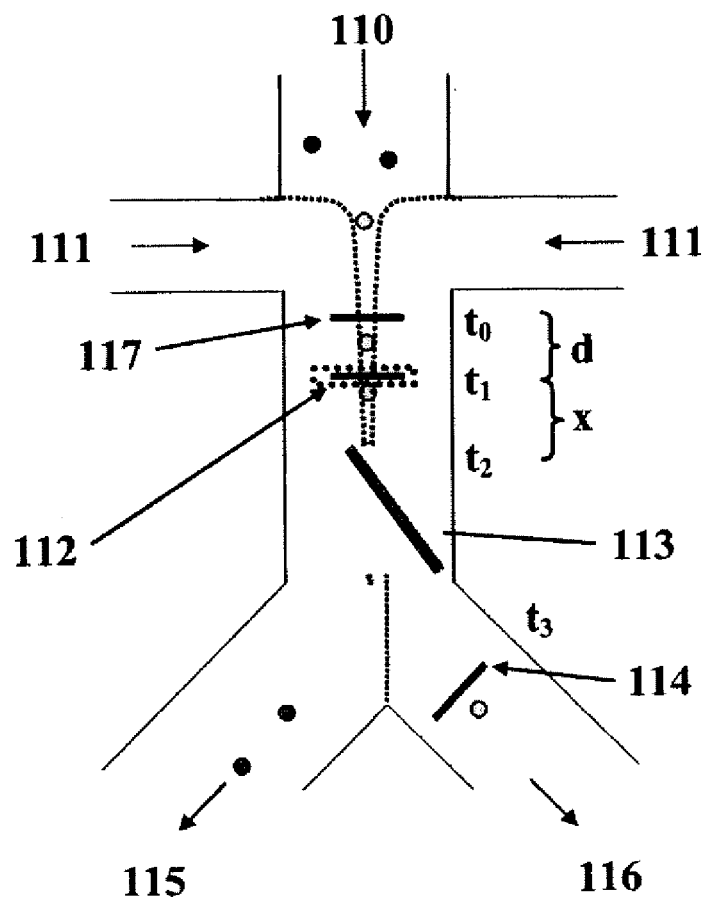
Figure 11D:
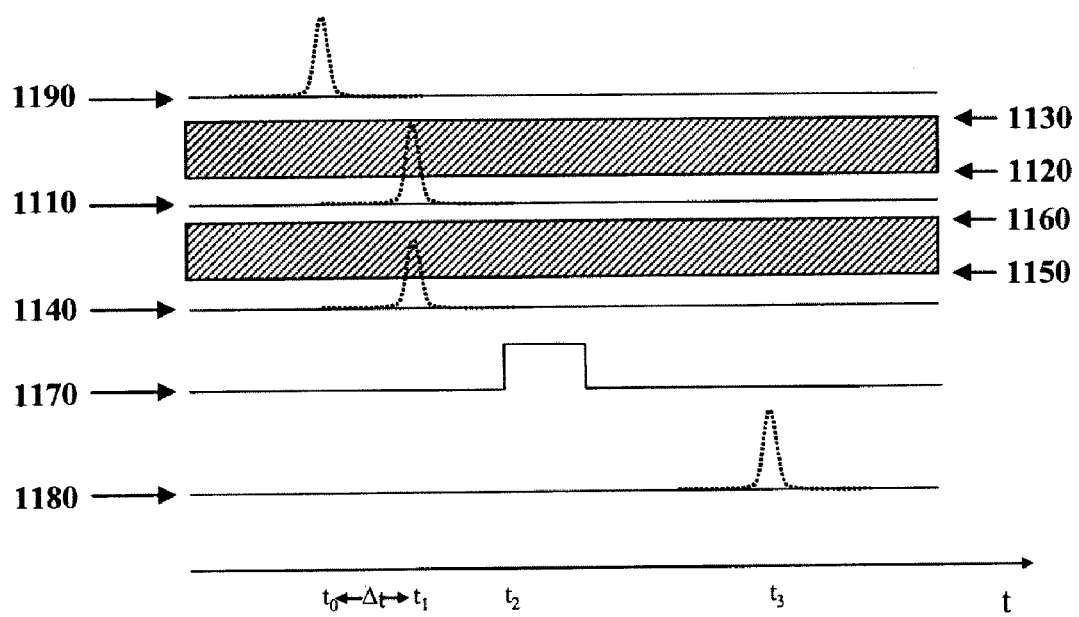

Alternatively, FIG. 11*c-d* show the detector arrangement and the timing/trigger diagram for when the sort parameter is positive and the optical switch is triggered. Here, the presence of a cell is again verified by the forward scatter signal 1190 (at time $t_0$) as it passes through the detection window region 117. As the cell passes through the identification/selection window 112 a second forward scatter signal 1110 which is between the gate limits 1120 and 1130 is obtained (at time $t_1$), and this signal is coupled with a fluorescence signal intensity 1140 (at time $t_1$) which is between the gating levels 1150 and 1160 and the optical switch 113 is triggered 1170 (at time $t_2$).

An error check signal 1180 (at time $t_3$) is now obtained since a cell was switched. In this approach the trigger time $t_2$ is not a preset value, but rather it is calculated using the cell stream flow rate (v) and the known distance (x) between the optical switch and the identification window. This is obtained using the relationships: $\Delta t=t_1-t_0$; $v=d/\Delta t$; $t_2=t_1+x/v$. This approach allows for more efficient sorting as it can account for fluctuations in cell flow rate, and therefore more accurately trigger the optical switch. An added benefit of this approach is, for each individual cell, the possibility of adjusting the rate at which the laser spot is translated down the channel such that it matches the velocity of the cell as determined above, thus maximizing the interaction time between the cell and the laser spot of the optical switch. The translation velocity of the laser spot would be varied by varying the driver for the AOM.

Another approach to improving the sorting efficiency, while incorporating the triggering approaches described above, is to centralize the cells in the main channel using channel designs which create a true sample core, whereby the core is completely surrounded by the sheath buffer. Variability in the location of a cell along the channel height can cause variability in cell detection and fluorescence intensity. Ensuring that the cells are in a core flowing in the center of the main channel may improve sorting efficiency, since this minimizes any variability due to radial distribution of cells, and controls the distance the cell needs to be moved to effect efficient sorting. Such a core flow can be achieved with a 2-dimensional pinch of the input flow stream with sheath buffer.

This approach requires a bottom substrate and a top substrate; each with microfluidic channel networks formed in them. FIG. 12*a-b* and FIG. 13 show one method to accomplish this, in which the channel design on one substrate is the mirror image of the design on the other substrate. Thus, when the two substrates are brought together, with the channel designs facing each other, the channel networks overlay and form complete fluidic conduits. FIG. 12*a-b* show one type of design used in this approach, with the sample channel 120 shown as a dashed line. The key feature of this approach is to ensure that the sample channels 120 are shallower than the sheath channels 121, such that when the substrates are brought together the sample conduit appears to enter the junction 122 as a hole. This is shown in FIG. 13, where the cells can be seen to enter the junction 132, and then are pinched from all sides creating a sample core which flows in the center of the main channel. Note that the channels can be formed by wet chemical etch or laser etch of glass or quartz, by molding or embossing in plastics or polymers.

Another method involves having a series of intersecting channels arranged such that in the first junction/intersection the cells are pushed vertically toward one wall of the main channel, the next junction/intersection forces this cell stream vertically into the center of the main channel, and then a final pinch flow from both sides at a third junction/intersection creates the complete sheath buffer shroud around a sample core flowing in the main channel. This is shown in FIG. 14 and FIG. 15, with one possible channel schematic shown in FIG. 16, where channels in the lower substrate are dashed and channels in the upper substrate are solid. In this example, at junction 141 sample flows from the top substrate into the junction and down into the channel in the bottom substrate, where the side sheath buffer flows into the junction from the sides. The sample is slightly focused and pushed to the top wall of the bottom channel as it continues to flow toward the next junction 142. Here a second sheath buffer flows into the junction 142 from the top substrate and the sample is pushed down to the middle of the channel in the bottom substrate. The sample continues to flow along the middle of the bottom channel toward the next junction 143. Here a third sheath buffer flows into junction 143 from both sides, and the sample is pinched into single file. The sample is now surrounded by sheath buffer as it continues to flow, as a sample core, centered both horizontally and vertically within the main input channel.

All of the microfluidic channel network designs described in FIGS. 1-16 have been produced in glass substrate utilizing conventional photolithographic masking and isotropic etching of the masked glass substrates. The isotropic etch typically produces microfluidic channels that have a depth $d_e$ at the center of the channel and a width $w=w_p+2 \times d_e$ at the top of the channel, where $w_p$ is the width of the photolithography pattern that defines the channel. The bottom profile of the channel has a quarter-round contour of radius $d_e$ at each edge due to the isotropic etch and the top of the etched channel is open. A glass substrate, typically a glass cover slip, is thermally bonded to the substrate with the etched microfluidic channels to seal the tops of the channels and complete a microfluidic channel network. Holes are typically drilled in the top substrate prior to the thermal bonding to provide vias for ingress and egress of fluid flow to the microfluidic channel network. The depth $d_e$ of the channels depends on the rate of the chemical etch process and the duration of the etch step. The depth of the microfluidic channels is typically in, but not limited to, the range 10 μm to 100 μm. The width of the microfluidic channels is typically, but not limited to, 2 to 5 times the depth. This is achieved by using lines on the photolithography mask that are typically, but not limited to, the range 5 μm to 400 μm. As mentioned previously, other substrates may be used, such as plastics or moldable or castable polymers. In these cases, the microfluidic channels typically have rectangular cross sections, but otherwise are similar to the channels in the glass substrates. The size of the glass substrate in which the microfluidic channel network is produced is typically in, but not limited to, the range of 5 mm×5 mm to 25 mm×50 mm with a total thickness in, but not limited to, the range 500 μm to 2 mm. The top substrate is typically the same size, with thickness in, but not limited to, the range 300 μm to 1 mm. The vias are typically, but not limited to, 200 μm to 600 μm in diameter. The completed substrate, with a microfluidic channel network and a bonded cover plate with vias for fluidic ports for ingress and egress of fluid flow, is termed a microfluidic sorting chip or chip for brevity.

The microfluidic channels networks shown in FIGS. 1-16 typically have only described the local geometries of the inlet microfluidic channel, the sheath buffer pinch junction channels, the cell identification and optical switch main channel, and the bifurcation of the main channel to the outlet channel. This description needs to be expanded to provide for regions in each channel to make the connections to reservoirs in a macro-scale fluidic device or cartridge that provides the interface to the vias described above to provide ingress and egress of the fluid flow from the network. The cross section and length of each of these microfluidic channels typically needs to be adjusted to assure appropriate controlled flow within the entire microfluidic channel network, depending on the technique selected to achieve the flow in the channels. Both the cross section and the length of these channels are determined by the pattern used to produce the photolithography mask.

FIG. 17 shows one embodiment of a mask for a complete microfluidic channel network that has an inlet channel, two sheath channels to a T-pinch junction and two outlet channels from a T-bifurcation junction. This mask was designed to provide a 7:1 volumetric pinch ratio (the sheath flow rate is seven times greater than the cell inlet flow rate). The length of the channels was designed to provide both sufficient pressure drop to enable the use of either standard low flow syringe pumps or low pressure pneumatic controllers to establish the flow. The design also reflects the balance of pressures needed to enable use of only two pumps, one for the cell inlet channel and one for the two sheath channels, with the outlets maintained at atmospheric pressure. The sheath channel inlet is at the termination at the top of the design, the cell inlet channel originates below this in the center of the two sheath channels and is long enough to provide the appropriate pressure drop to set the 7:1 pinch ratio, and the two outlets are located at the termini at the bottom left and right.

FIG. 18 shows another embodiment that incorporates a triangular junction for the pinch junction and a Y-bifurcation junction, in a design that provides a 10:1 volumetric pinch ratio. Otherwise the design is geometrically similar to that of FIG. 17. Many other designs are clearly possible, but they all share the common features of needing to provide for fluidic ingress and egress and to provide appropriate pressure drops and pressure balances for the method chosen to establish the fluid flow. Similar design conditions are used to produce the photolithography masks used to make the microfluidic channel networks for 2-dimensional pinch flow networks described previously.

FIG. 19 shows a preferred embodiment of a microfluidic channel network in a completed microfluidic sorting chip. The two inlet ports, for the cell sample flow 190 and for the sheath buffer flow 191 are identified, as are the two outlet ports, for the fluorescence-positive target cells 192 and for the fluorescence-negative non-target cells 193, the waste stream. The chip is 24 mm by 40 mm. The thickness of the etched substrate is 1.1 mm. The thickness of the bonded cover plate is 550 μm. The microfluidic channels are 50 μm deep. The cell inlet microfluidic channel is 110 μm wide. The sheath flow and outlet microfluidic channels are 150 μm wide, as is the main microfluidic channel. The sheath flow pinch junction is an inverted equilateral triangle, 300 μm per side, connecting the cell inlet channel through the base of the triangle, at the top of the junction, with the two sheath flow pinch channels from each side to the main channel through the apex of the triangle, at the bottom of the junction. This microfluidic channel network design is optimized to use pneumatic control of the flow at all four ports to establish the network flow.

Microfluidic connections to the chip may be made in a variety of ways. One method is to use flexible microfluidic tubing directly connected to the ports, either by gluing or using various tubing adapters that can be attached to the surface of the chip at the ports. This tubing can be connected directly to syringe pumps or similar systems that provide volumes for handling both the cell sample and the sheath buffers and provide the pressure to flow these volumes through the chip. Using the syringe pumps for handling the sample volume requires that the pump be cleaned and reloaded for each sample and introduces the possibility for carry over or contamination from one sample to the next.

An improved method for microfluidic connections to the chip utilizes a cartridge that is directly adhered to the chip using a UV-curable adhesive, a PSA bonding sheet, or other conventional bonding methods. The cartridge has four built-in reservoirs that separately provide interface connections to the cell inlet channel, the two sheath channels (from one reservoir), and each of the two outlet channels. Such a cartridge provides the possibility of sterile handling of both the cell sample and the sorted target cells and waste stream, since they can be completely confined to the volumes of the cartridge before and after the cell sort. The flow for such a cartridge and chip system can be provided by using two pneumatic pressure controllers that separately pressurize the cell inlet and sheath buffer reservoirs to induce flow through the microfluidic channel network of the chip to the outlet reservoirs that are at atmospheric pressure.

An improved flow control method is provided by using four pneumatic controllers that separately pressurize each of the cell inlet, sheath buffer, target cell collection and waste collection reservoirs. Such a flow control system provides the ability to separately adjust the volumetric pinch ratio at the sheath pinch junction, the flow velocity of the cells in the main microfluidic channel for the fluorescence analysis and optical switch, and the split ratio at the switching bifurcation to enable biased flow, as described previously.

FIG. 20 shows a preferred embodiment of a self-contained disposable cartridge 210 that provides fluidic reservoirs for the cell sample volume 200, the sheath buffer volume 201 and the two outlet collection volumes 202 for target cells and waste respectively. The cartridge 210 is manufactured from acrylic plastic and may either be machined or cast. Other plastics or suitable materials may be substituted for acrylic if appropriate. The cell sample volume 200 is typically conical in shape, tapering towards the port to the inlet microfluidic channel 191. In the preferred embodiment, the inlet reservoir contains a polypropylene insert to minimize cell adhesion and consequently maximize cell yield. The chip is bonded with UV adhesive to the optical window region 203, and the outlet ports from the chip interface with their respective reservoir volumes. The reservoir volumes 200, 201, 202 are sealed with the snap-on lid 204 that has drilled ports for connection between the pneumatic controllers and the individual reservoirs 200, 201, 202. The lid 204 contains a silicone gasket to aid in sealing against the cartridge body 210. It also incorporates a 0.1 μm polypropylene filter to create a gas permeable, liquid tight interface between the cartridge volumes and the external environment. This maintains aseptic conditions on the cartridge and minimizes any biohazard contamination to the user or the instrument.

The cartridge 210 is prepared for a cell sorting run by first priming the microfluidic channel network through the sheath port with sheath buffer solution, using an ordinary syringe with a luer fitting. In this way the channels are primed and the sheath reservoir 201 is filled with 800 μl and each outlet reservoir 202 is filled with 200 μl. The cell sample reservoir 200 is aspirated of excess buffer liquid and then 5-25 μl of cell sample is placed into the sample input reservoir 200 using a pipette. The cartridge lid 204 is then applied and snapped into place, providing a self-contained system in which to perform the cell sorting run.

The cartridge 210 is designed to be placed in a holder that positions the main channel 190 of the chip such that the optical imaging system that projects the optical switch beam into the channel is appropriately aligned and focused into the channel 190. The cartridge holder also includes a pressure manifold plate that has four ports, connected by external tubing to the four pneumatic controllers 211. Each manifold port is sealed to its respective cartridge lid port with an o-ring, and these seals are made leak free by pressing the manifold against the cartridge lid with a cam-lock mechanism.

A preferred embodiment of the optical system for the optical switch is shown in FIG. 21. The cartridge 210, with the pneumatic manifold 211 connecting to the snap-on lid 204, is positioned such that the optical switch region is at the focus of both a lens system viewing from above 212, 215 the cartridge and a lens system viewing from below 213, 221. The output beam from a 488 nm laser 214 is projected through the imaging system 212, 215 into the main channel just upstream of the sorting region, as shown in FIGS. 3-7 and 9-11, to provide excitation for the detection of fluorescence from fluorescence-positive target cells. The fluorescence emission is collected by the same lens and imaged through a dichroic mirror and an appropriate fluorescence emission filter to a photomultiplier tube. The signal from the photomultiplier tube 217 is processed by the electronics to measure the level of the fluorescence from the cells and determine the presence of fluorescence-positive target cells in the flow stream in the main channel. The fluorescence excitation is not limited to the 488 nm wavelength, but can be at any wavelength that is appropriate for the fluorophores used to identify the target cells. If a different excitation illumination is used, the wavelength of the fluorescence emission filter must be changed accordingly. When fluorescence-positive cells are identified, the electronics triggers the AOM 219 to direct the beam from the IR-laser, 220, typically a 1070 nm laser operation between 5 W and 20 W output power, into the main channel at the optical switch position. In the preferred embodiment, the AOM 219 is controlled to produce an optical switch pattern as described in FIG. 9b, although any of the optical switch methods previously described could be implemented. The lens 213 below the cartridge 210 images the 488 nm excitation illumination onto a photodiode 223. The signal detected by this photodiode 223 is used to help distinguish fluorescently labeled cells from smaller debris that may carry the fluorescent label, and also to identify clumps of cells that might have formed. These events are rejected as candidates for sorting to the target output channel.

Yet another preferred embodiment would incorporate appropriate imaging and optical filtering to provide a forward scattering signal based on the illumination of the cell by the 488 nm laser that is used to excite the fluorescence. The optics would provide a range of angular sensitivity, such as, but not limited to this range, 0.8° to 10°, for the detection of the forward scattering signal. This signal can help characterize cells in addition to the fluorescence signal, as well as help distinguish cells from debris. The forward scattering illumination is not limited to the fluorescence excitation laser, but could be at any other wavelength provided by an additional light source that is properly imaged into the main channel.

Yet another preferred embodiment would incorporate additional fluorescence detection channels that are sensitive to fluorescence emissions at different wavelength, typically using a single excitation wavelength, such as, but not limited to, 488 nm. Each detection channel would incorporate a PMT with an appropriate dichroic mirror and emission filter for the fluorescence emission wavelength of the additional fluorophore. From two to four fluorescence detection channels are readily accommodated in this manner. Using more than one fluorophore in this manner provides the ability for multiple detection criteria to identify the target cells for sorting with the optical switch.

Yet another preferred embodiment would incorporate an error checking capability that provides optical illumination, typically as a narrow line across one of the channels in the network, and typically at a longer wavelength, perhaps, but not limited to, 785 nm from a solid state laser, that is outside the range of wavelengths used for fluorescence detection and forward scatter detection, but is shorter than the optical switch wavelength that is typically at 1070 nm. This source can be appropriately imaged into the microfluidic channel network to provide lines that can be used to detect passage of particles through any vertical plane in the network. This provides additional ability to check the performance of the optical switch performance and provides additional capability for the timing of the trigger of the optical switch, as described in FIG. 11.

Yet another preferred embodiment of the optical system would incorporate an additional optical illumination path at, but not restricted to, 750 nm, e.g., as produced by band pass filtering the light from an LED, and illuminating a region of the microfluidic channels with that light. That region would be imaged through a 750 nm pass filter onto a CCD camera to provide visualization of the performance of the cells flowing in the microfluidic channel network at the bifurcation junction and/or at the pinch junction. The filters before the camera would be adequate to block any shorter wavelength radiation associated with the excitation or detection of fluorescence and with the forward/side scatter optics and the error detection optics. The filters would also block the longer wavelength, 1070 nm light from the optical switch.

The preferred embodiment of the cartridge 210 shown in FIG. 20 is designed to hold the microfluidic channel network in a horizontal configuration, so that all of the channels and inlet/outlet ports are at the same vertical level. This minimizes the effects of gravity on the pressure drops through the microfluidic channels, leading to more stable and controllable flow in the network. However, gravity will still have an effect on the cells in the flow, particularly as the cells pass from the cell sample reservoir into the cell inlet microfluidic channel. Another preferred embodiment of the sorter, to help control the effects of gravity on settling of the cells in this reservoir and on their settling in the relatively slower flow in the inlet microfluidic channel before the cells flow speeds up at the pinch junction, is to enhance the buoyancy of the cells, such that settling of the cells is minimized. Increasing the buoyancy can be achieved by using additives in the sample buffer. Examples of these rheological control additives, particularly those that are either pseudoplastic or shear thinning, or both, are xanthan gum, carageenan, sodium carboxymethylcellulose, methylcellulose, hydroxypropylmethylcellulose, hydroxyethylcellulose, hydroxypropylcellulose, hydroxypropyl guar, Gum Arabic, Gum Tragacanth, Alginate, polyacrylates, carbomer. Other additives include Histopaque™, which is a mixture of polysucrose and sodium diatrizoate, and Optiprep™, which is a 60% w/v solution of iodixanol in water. The concentration of these additives used depends on the density of the cell being sorted. For instance, in the case of Optiprep™ the concentration can range from 5% to 40%. Finally, salinity of the sample buffer and addition of sucrose can also be used to adjust the buoyancy of cells.

The buffers that are used for the cell sample volume and for the sheath flow can be any buffers that are biologically compatible with the cells that are being sorted, and are compatible with optical illumination that is used both for the fluorescence detection modality and for the optical switch, i.e., the buffer has sufficiently low absorbance at the fluorescence excitation/detection wavelengths and the optical switch wavelength. A preferred embodiment of the sheath buffer uses PBS/BSA, phosphate buffered saline (PBS) at pH 7.2 with 1% bovine serum albumin (BSA) fraction 5. A preferred embodiment of the cell buffer uses PBS/BSA with 14.5% Optiprep for live cell samples and 27% Optiprep for a variety of formalin fixed cell samples.

The performance of the optical switch method of cell sorting in a microfluidic, channel network is evaluated by the throughput, purity and recovery of the sort as previously described. The cartridge described in FIG. 20 is optimized to allow measurement of the performance, since the bottoms of the target and waste collection reservoirs are transparent and the cells that are sorted into these reservoirs can be quantified as to both number and fluorescence labeling using an inverted fluorescence microscope. Several of the switching configurations described in FIGS. 3-11 were evaluated. These evaluations were performed using a 50:50 mix of live HeLa:HeLa-GFP cells that was sorted using either a 1- or 2-sided stationary laser spot, or a 0° or 8° 1-sided laser sweep. The laser was swept at 240 Hz. The laser ON time was 4 msec and the laser power was 20 W for all switch modes. For the swept spot method, the focused IR laser spot was translated about 70 μm along the main channel.

As shown in FIG. 22, the bi-directional optical switch with laser spots, described in FIG. 6, gave good results for purity and recovery for the 50:50 mixes of target:non-target cells up to a throughput of 50 cells/s. However, at lower subpopulation concentrations (data not shown), it was not an efficient use of laser power to switch non-target cells, and coincidence errors increased at higher cell throughput rates. Additionally, small particulates that were not switched would contaminate the target reservoir.

FIG. 22 also shows the performance of the 1-sided switching methods, described in FIG. 9, with a stationary laser spot or a spot that is translated in the direction of flow, either parallel or at a slight angle to the flow. The sample core flow stream was biased to the waste outlet such that all the cells went to waste by default in the absence of the optical switch. Both of these methods gave improved performance, as shown by the plots. The fact that the performance of these two methods crosses, suggests that the triggering of the optical switch was not optimal, and suggests that the active triggering of the optical switch as described in FIGS. 10 and 11 will improve performance.

ENDNOTES

1. H. M. Shapiro, *Practical flow cytometry*, Wiley-Liss, New York, 2003.
2. Y. Fu, C. Spence, A. Scherer, F. H. Arnold and S. R. A. Quake, "Microfabricated fluorescence-activated cell sorter," *Nat. Biotechnol.* 17, pp. 1109-1111, 1999.
3. Y. Fu, H.-P. Chou, C. Spence, F. H. Arnold, and S. R. Quake, "An integrated microfabricated cell sorter," *Anal. Chem.* 74, pp. 2451-2457, 2002.
4. Wolff, I. R. Perch-Nielsen, U. D. Larsen, P. Friis, G. Goranovic, C. R. Poulsen, J. P. Kutter and P. Telleman, "Integrating advanced functionality in a microfabricated high-throughput fluorescent-activated cell sorter," *Lab Chip* 3, pp. 22-27, 2003
5. Li, P. C. H. & Harrison, D. J. Transport, manipulation, and reaction of biological cells on-chip using electrokinetic effects. *Anal. Chem.* 69, 1564-1568 (1997).
6. Dittrich, P. S. & Schwille, P. An integrated microfluidic system for reaction, high-sensitivity detection, and sorting of fluorescent cells and particles. *Anal. Chem.* 75, 5767-5774 (2003).

7. Fiedler, S., Shirley, S. G., Schnelle, T. & Fuhr, G. Dielectrophoretic sorting of particles and cells in a microsystem. *Anal. Chem.* 70, 1909-1915 (1998).
8. Y. Huang, K. L. Ewalt, M. Tirado, R. Haigis, A. Forster, D. Ackley, M. J. Heller, J. P. O'Connell, M. T. Krihak, "Electric manipulation of bioparticles and macromolecules on microfabricated electrodes," *Anal. Chem.* 73, pp. 1549-1559, 2001.
9. M. Durr, J. Kentsch, T. Muller, T. Schnelle and M. Stelzle, "Microdevices for manipulation and accumulation of micro- and nanoparticles by dielectrophoresis," *Electrophoresis* 24, pp. 722-731, 2003.
10. T. N. Buican, M. J. Smyth, H. A. Crissman, G. C. Salzman, C. C. Stewart and J. C. Martin, "Automated single-cell manipulation and sorting by light trapping," *Appl. Opt.* 26, pp. 5311-5316, 1987.

We claim:

1. An integrated structure for microfluidic analysis and sorting comprising:
   a cartridge, the cartridge comprising
      an optical window,
      a plurality of reservoirs, including at least:
         a sample reservoir,
         a fluid reservoir,
         a waste reservoir, and
         a target collection reservoir,
   a chip, the chip including at least:
      a sample inlet channel, the cell inlet channel being fluidically coupled to the sample reservoir,
      one or more fluid inlet channels, the fluid inlet channels being fluidically coupled to the fluid reservoir,
      a detection region,
      a branched sorting region, and
      at least two outlet channels including at least a waste channel and a target channel, waste channel being fluidically coupled to the waste reservoir and the target channel being coupled to the target collection reservoir,
      the chip being disposed adjacent the optical window, and
   a lid, the lid including at least:
      a pneumatic pressure port, the port having an inlet and being coupled to at least one of the sample reservoir and the fluid reservoir, and
      a filter disposed between the inlet of the pneumatic pressure port and at least one of the sample reservoir and the fluid reservoir,
   a detector adapted to detect cells of a given state and to generate a signal in response thereto, and
   a lateral force switch coupled to the detector and actuatable in response to the signal, the lateral force switch comprising a laser spot configured to be translated down the length of the detection region at an angle relative to a flow stream through the detection region;
   whereby when a cell of a given state is detected, the lateral force switch is activated to sweep the laser spot alongside the cell as it flows to provide a lateral force on the cell so as to move the cell such that it selectively exits into the one of the at least two outlet channels.
2. The integrated structure for microfluidic analysis and sorting of claim 1 wherein the sample reservoir is conical.
3. The integrated structure for microfluidic analysis and sorting of claim 1 wherein the sample reservoir is tapered.
4. The integrated structure for microfluidic analysis and sorting of claim 1 wherein the sample reservoir further includes an insert.
5. The integrated structure for microfluidic analysis and sorting of claim 1 wherein the insert is a polypropylene insert.
6. The integrated structure for microfluidic analysis and sorting of claim 1 wherein the lid is plastic.
7. The integrated structure for microfluidic analysis and sorting of claim 6 wherein the lid is acrylic plastic.
8. The integrated structure for microfluidic analysis and sorting of claim 1 wherein the lid includes separate pneumatic pressure ports for the sample reservoir and the fluid reservoir.
9. The integrated structure for microfluidic analysis and sorting of claim 8 wherein the lid includes a pneumatic pressure port for the target collection reservoir.
10. The integrated structure for microfluidic analysis and sorting of claim 8 wherein the lid includes a pneumatic pressure port for the waste reservoir.
11. The integrated structure for microfluidic analysis and sorting of claim 1 wherein the lid includes a pneumatic pressure port for the target collection reservoir.
12. The integrated structure for microfluidic analysis and sorting of claim 1 wherein the lid includes a pneumatic pressure port for the waste reservoir.
13. The integrated structure for microfluidic analysis and sorting of claim 1 wherein the lid provides optical access to the reservoirs.
14. The integrated structure for microfluidic analysis and sorting of claim 1 wherein the lid includes snap-on attachments to couple to the cartridge.
15. The integrated structure for microfluidic analysis and sorting of claim 1 wherein the filter is gas permeable.
16. The integrated structure for microfluidic analysis and sorting of claim 15 wherein the filter is fluid impermeable.
17. The integrated structure for microfluidic analysis and sorting of claim 1 wherein the filter is fluid impermeable.
18. The integrated structure for microfluidic analysis and sorting of claim 1 wherein the filter is a polypropylene filter.
19. The integrated structure for microfluidic analysis and sorting of claim 1 wherein curable adhesive is disposed between the chip and the cartridge.
20. The integrated structure for microfluidic analysis and sorting of claim 1 wherein the adhesive is UV curable.
21. The integrated structure for microfluidic analysis and sorting of claim 1 further including a bonding sheet between the chip and the cartridge.
22. The integrated structure for microfluidic analysis and sorting of claim 21 wherein the bonding sheet is a pressure sensitive adhesive.
23. The integrated structure for microfluidic analysis and sorting of claim 1 wherein optical access to the chip is provided through the optical window and through the reverse side of the chip.
24. The integrated structure for microfluidic analysis and sorting of claim 1 wherein the sample reservoir is adapted to contain from 10 to 30 microliters.
25. The integrated structure for microfluidic analysis and sorting of claim 1 wherein the fluid reservoir is adapted to contain 500 to 1,500 microliters.
26. The integrated structure for microfluidic analysis and sorting of claim 1 further including a gasket between the lid and cartridge.
27. The integrated structure for microfluidic analysis and sorting of claim 1 wherein the waste reservoir contains non-target materials.
28. The integrated structure for microfluidic analysis and sorting of claim 1 wherein the waste reservoir contains excess fluid.
29. The integrated structure for microfluidic analysis and sorting of claim 1 wherein the chip and cartridge comprise two separate structures.

30. A method for cell sorting in a device having an inlet, a fluidically coupled channel, and at least two fluidically coupled outputs, comprising the steps of:
   receiving a cell in a fluidic medium at an inlet,
   flowing the cell through a fluidic channel,
   subjecting the cell to a bias flow resulting in collection in a first reservoir,
   identifying a cell to be sorted through application of a lateral force into a second reservoir, and
   applying a lateral force on the cell, the lateral force comprising a laser spot configured to be translated at a non-zero angle down the fluidic channel toward the at least two outputs and characterized in that the lateral force is a non-trapping force and in that the lateral force is moved alongside a selected cell as it flows down the fluidic channel, thereby increasing the total interaction time between the lateral force and the cell, whereby the cell selectively exits into the outlets.

31. The method for cell sorting of claim 30 wherein the laser illumination is moved linearly along the channel in proximity to the cell as it flows through the channel.

32. The method for cell sorting of claim 30 wherein the laser illumination is moved diagonally along the channel in proximity to the cell as it flows through the channel.

* * * * *